US012329855B2

(12) United States Patent
Khang et al.

(10) Patent No.: US 12,329,855 B2
(45) Date of Patent: Jun. 17, 2025

(54) DRUG DELIVERY SYSTEM WITH ENHANCED IMMUNE ACTIVE FUNCTION

(71) Applicants: Gachon University of Industry-Academic Cooperation Foundation, Gyeonggi-do (KR); RUDACURE Corporation, Incheon (KR)

(72) Inventors: Dongwoo Khang, Seoul (KR); Sung Jean Park, Incheon (KR); Jun-Young Park, Incheon (KR); Jun Young Park, Gyeonggi-do (KR)

(73) Assignees: Gachon University of Industry-Academic Cooperation Foundation, Gyeonggi-do (KR); RUDACURE Corporation, Incheon (KR)

( * ) Notice: Subject to any disclaimer, the term of this patent is extended or adjusted under 35 U.S.C. 154(b) by 0 days.

(21) Appl. No.: 17/485,686

(22) Filed: Sep. 27, 2021

(65) Prior Publication Data
US 2023/0172850 A1      Jun. 8, 2023

(51) Int. Cl.
*A61K 9/00*     (2006.01)
*A61K 45/06*    (2006.01)
*A61K 47/10*    (2017.01)
*A61K 47/42*    (2017.01)

(52) U.S. Cl.
CPC ............ *A61K 9/0092* (2013.01); *A61K 45/06* (2013.01); *A61K 47/10* (2013.01); *A61K 47/42* (2013.01)

(58) Field of Classification Search
CPC ............ A61K 47/6929; A61K 38/1774; A61K 47/64; A61K 9/0092; A61K 2039/505; A61K 39/44; A61P 35/00
See application file for complete search history.

(56) References Cited

U.S. PATENT DOCUMENTS

2002/0146449 A1* 10/2002 Wong ................. A61K 38/16
                                                514/19.3
2016/0159826 A1*  6/2016 Lai .................. C08F 112/08
                                                525/333.6

OTHER PUBLICATIONS

Scott-Taylor, "Immunoglobulin G; structure and functional implications of different subclass modifications in initiation and resolution of allergy", Immunity, Inflammation and Disease, 6(1), pp. 13-33, Mar. 2018 (Year: 2018).*
Schroeder , "Structure and function of immunoglobulins", J Allergy Clin Immunol, pp. S41-S52, Feb. 2010 (Year: 2010).*
Bartneck, et al., "Rapid Uptake of Gold Nanorods by Primary Human Blood Phagocytes and Immunomodulatory Effects of Surface Chemistry" ACS Nano, vol. 4 ■ No. 6 ■ 3073-3086 ■ 2010.
Caracciolo, et al., "Biological Idetnity of Nanoparticles in Vivo; Clinical Implications of the Protein Corona" Trends Biotechnol., 2017 Marc; 35(3):257-264.
Deng, et al. "Nanoparticle-induced unfolding of fibrinogen promotes Mac-1 receptor activation and inflammation" Nature Nanotechnology, vol. 6, Jan. 2011, pp. 39-44.
Duan et al., "Fluorescamine Labeling for Assessment of Protein Conformational Change and Binding Affinity in Protein-Nanoparticle Interaction" Anal Chem. Nov. 2, 20171; 89(22): 12160-12167.
Lee et al. "Effect of the protein corona on nanoparticles for modulating cytotoxicity and immunotoxicity" International Journal of Nanomedicine 2015:10 97-113.
Lesniak, et al. "Effects of the Presence or Absence of a Protein Corona on Silica Nanoparticle Uptake and Impact on Cells" vol. 6, No. 7, 5845-5857, 2012, ACS Nano.
Raouf, et al. "Probing Fibronectin Conformation on Protein Corona Layer around Nanoparticles" Nanoscale 2018 Jan. 2018;10(3) 1228-1233.
Smith et al. "Applications of nanotechnology for immunology" Nature Reviews Immunology, vol. 13, Aug. 2013.
Vlasova, et al. "Adsorbed plasma proteins modulate the effects of single-walled carbon nanotubes on neutrophils in blood" Nanomedicine: NBM 2016;12:1615-1625.
Author Unknown, "a1-Acid Glycoprotein for human plasma" 2023, 9 pages Merck, KgaA.
Hochepied "a1-Acid glycoprotein: an acute phase protein with inflammatory and immunomodulating properties" Cytokine & Growth Factor Reviews 14 (2003) 25-34.
Bhushan O. Murjani, et al., "Carbon nanotubes in biomedical applications: current status, promises, and challenges", Carbon Letters, Jul. 4, 2022, pp. 1207-1226, (2022) 32, https://doi.org/10.1007/s42823-022-00364-4.
Hua He et al., "Carbon Nanotubes: Applications in Pharmacy and Medicine", Jul. 26, 2013, Hindawi Publishing Corporation, BioMed Research International, 12 pp., vol. 2013, Article ID 578290, http://dx.doi.org/10.1155/2013/578290.

\* cited by examiner

*Primary Examiner* — Nicole P Babson
*Assistant Examiner* — John P Nguyen
(74) *Attorney, Agent, or Firm* — Stuart H. Mayer; Kaplan Breyer Schwarz LLP

(57) ABSTRACT

Provided is a composite nanoparticle in which an immunogenic plasma protein is coated on the surface of the nanoparticle due to the enhanced immune activity function caused by structural changes in immunogenic protein coronas.

7 Claims, 23 Drawing Sheets
Specification includes a Sequence Listing.

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: Il6 F

<400> SEQUENCE: 1
atcttctcct gggggtactg                                               20

<210> SEQ ID NO 2
<211> LENGTH: 20
<212> TYPE: DNA
<213> ORGANISM: Artificial Sequence
<220> FEATURE:
<223> OTHER INFORMATION: Il6 R

<400> SEQUENCE: 2 cttttctgc aggaactgga                                                20

<210> SEQ ID NO 3
<211> LENGTH: 20
<212> TYPE: DNA
<213> ORGANISM: Artificial Sequence
<220> FEATURE:
<223> OTHER INFORMATION: Tnf F

<400> SEQUENCE: 3
cctaccagac caaggtcaac                                               20

<210> SEQ ID NO 4
<211> LENGTH: 20
<212> TYPE: DNA
<213> ORGANISM: Artificial Sequence
<220> FEATURE:
<223> OTHER INFORMATION: Tnf R

<400> SEQUENCE: 4 aggggtaat aaagggattg                                                20
```

```
<210> SEQ ID NO 5
<211> LENGTH: 20
<212> TYPE: DNA
<213> ORGANISM: Artificial Sequence
<220> FEATURE:
<223> OTHER INFORMATION: Il1b F

<400> SEQUENCE: 5
ccagctgtag agtgggctta                                               20

<210> SEQ ID NO 6
<211> LENGTH: 20
<212> TYPE: DNA
<213> ORGANISM: Artificial Sequence
<220> FEATURE:
<223> OTHER INFORMATION: Il1b R

<400> SEQUENCE: 6
ggatatggag caacaagtgg                                               20

<210> SEQ ID NO 7
<211> LENGTH: 24
<212> TYPE: DNA
<213> ORGANISM: Artificial Sequence
<220> FEATURE:
<223> OTHER INFORMATION: GAPDH F

<400> SEQUENCE: 7
gtatgacaac gaatttggct acag                                          24

<210> SEQ ID NO 8
<211> LENGTH: 24
<212> TYPE: DNA
<213> ORGANISM: Artificial Sequence
<220> FEATURE:
<223> OTHER INFORMATION: GAPDH R

<400> SEQUENCE: 8
tctctctctt cctcttgtgc tctt                                          24

<210> SEQ ID NO 9
<211> LENGTH: 23
<212> TYPE: DNA
<213> ORGANISM: Artificial Sequence
<220> FEATURE:
<223> OTHER INFORMATION: Il6 F

<400> SEQUENCE: 9
tagtccttcc taccccaatt tcc                                           23

<210> SEQ ID NO 10
<211> LENGTH: 20
<212> TYPE: DNA
<213> ORGANISM: Artificial Sequence
<220> FEATURE:
<223> OTHER INFORMATION: Il6 R

<400> SEQUENCE: 10
tggtccttag ccactccttc                                               20

<210> SEQ ID NO 11
<211> LENGTH: 19
<212> TYPE: DNA
<213> ORGANISM: Artificial Sequence
<220> FEATURE:
<223> OTHER INFORMATION: Tnf F
```

```
<400> SEQUENCE: 11
cctgtagccc acgtcgtag                                                19

<210> SEQ ID NO 12
<211> LENGTH: 22
<212> TYPE: DNA
<213> ORGANISM: Artificial Sequence
<220> FEATURE:
<223> OTHER INFORMATION: Tnf R

<400> SEQUENCE: 12
gggagtagac aaggtacaac cc                                            22

<210> SEQ ID NO 13
<211> LENGTH: 22
<212> TYPE: DNA
<213> ORGANISM: Artificial Sequence
<220> FEATURE:
<223> OTHER INFORMATION: Il1b F

<400> SEQUENCE: 13
gcaactgttc ctgaactcaa ct                                            22

<210> SEQ ID NO 14
<211> LENGTH: 21
<212> TYPE: DNA
<213> ORGANISM: Artificial Sequence
<220> FEATURE:
<223> OTHER INFORMATION: Il1b R

<400> SEQUENCE: 14
atcttttggg gtccgtcaac t                                             21

<210> SEQ ID NO 15
<211> LENGTH: 24
<212> TYPE: DNA
<213> ORGANISM: Artificial Sequence
<220> FEATURE:
<223> OTHER INFORMATION: Il4 F

<400> SEQUENCE: 15
ctgtagggct tccaaggtgc ttcg                                          24

<210> SEQ ID NO 16
<211> LENGTH: 24
<212> TYPE: DNA
<213> ORGANISM: Artificial Sequence
<220> FEATURE:
<223> OTHER INFORMATION: Il4 R

<400> SEQUENCE: 16
ccatttgcat gatgctcttt aggc                                          24

<210> SEQ ID NO 17
<211> LENGTH: 19
<212> TYPE: DNA
<213> ORGANISM: Artificial Sequence
<220> FEATURE:
<223> OTHER INFORMATION: Il13 F

<400> SEQUENCE: 17
cctggctctt gcttgcctt                                                19

<210> SEQ ID NO 18
<211> LENGTH: 21
```

-continued

```
<212> TYPE: DNA
<213> ORGANISM: Artificial Sequence
<220> FEATURE:
<223> OTHER INFORMATION: Il13 R

<400> SEQUENCE: 18
ggtcttgtgt gatgttgctc a                                             21

<210> SEQ ID NO 19
<211> LENGTH: 21
<212> TYPE: DNA
<213> ORGANISM: Artificial Sequence
<220> FEATURE:
<223> OTHER INFORMATION: Infg F

<400> SEQUENCE: 19
atgaacgcta cacactgcat c                                             21

<210> SEQ ID NO 20
<211> LENGTH: 21
<212> TYPE: DNA
<213> ORGANISM: Artificial Sequence
<220> FEATURE:
<223> OTHER INFORMATION: Infg R

<400> SEQUENCE: 20
ccatcctttt gccagttcct c                                             21

<210> SEQ ID NO 21
<211> LENGTH: 20
<212> TYPE: DNA
<213> ORGANISM: Artificial Sequence
<220> FEATURE:
<223> OTHER INFORMATION: GAPDH F

<400> SEQUENCE: 21
ctggtatgac aatgaatacg                                               20

<210> SEQ ID NO 22
<211> LENGTH: 20
<212> TYPE: DNA
<213> ORGANISM: Artificial Sequence
<220> FEATURE:
<223> OTHER INFORMATION: GAPDH R

<400> SEQUENCE: 22
gcagcgaact ttattgatgg                                               20
```

DRUG DELIVERY SYSTEM WITH ENHANCED IMMUNE ACTIVE FUNCTION

BACKGROUND

The present disclosure relates to a drug delivery system, and more particularly, to a drug delivery system with an enhanced immune activity function.

The clinical application of drug delivery systems based on nanoparticles (hereinafter abbreviated as "NP") raises many concerns from immunological and toxicological points of view (D. M. Smith, et al., *Nat Rev Immunol*, 13, 592. 2013). In particular, the immune response by corona, which is a foreign protein formed after NP injection from the bloodstream, is very important because it needs to be clarified prior to its clinical application (G. Caracciolo, et al., *Trends Biotechnol*, 35, 257. 2017). Since many plasma proteins interact with NPs, a newly formed protein corona around NPs can affect the activation of an immune system (Z. J. Deng, et al., *Nat Nanotechnol.*, 6, 39. 2011). These interactions between NPs and plasma proteins can induce structural changes that are highly dependent on the physicochemical properties of NPs, and the altered structure of plasma proteins can directly affect subsequent immune responses (M. Bartneck, et al., *J. Groll, ACS Nano*, 4, 3073. 2010). In this regard, it is important to analyze the structural changes of the protein corona around NPs and examine their effects on immunotoxicity, and this can provide important guidelines for predicting the unwanted nanotoxicity caused by the formation of the undesirable protein corona around NPs.

Traditionally, "hard" corona (proteins bound with high affinity) has been considered more important than "soft" corona (weak affinity for NPs) (Y. K. Lee, et al., *Int J Nanomedicine*, 10:97, 2015). Therefore, since a long retention time increases the probability of uptake by immune cells in the plasma, immune cells are mainly regarded as hard corona (A. Lesniak, et al., *ACS Nano*, 6, 5845. 2012). In fact, since the plasma protein corona around the NPs is very transient and deforms within a very short period of time, it is very difficult to observe the immunological effects of the specific protein corona surrounding NPs. Inevitably, the examination of the immune responses elicited by a stable and constant type of a specific protein in NPs is essential to understanding the immunological effects of corona proteins around NPs. Consequently, the analysis of the type-dependent structural changes of plasma proteins induced by NPs and elucidating their relationship with the immune system could provide deeper insights into the mechanisms of differential responses of human plasma proteins to NPs. Recent studies have reported that NPs have an important role to determine structural changes of corona proteins and subsequent cellular interactions (Y. Duan, et al., *Anal Chem*, 89, 12160. 2017). However, almost no studies have been conducted on the immune responses relating to the structural changes of the protein corona surrounding NPs nor they have been studied comprehensively (M. Raoufi, et al., *Nanoscale*, 10, 1228. 2018).

SUMMARY

However, the study on the nanomaterial-protein corona interactions according to the structural changes in plasma proteins in the immune response in vivo is still an unexplored field.

The present disclosure is intended to solve several challenges including the issues described above, and a purpose of the present disclosure is to provide a drug delivery system with an enhanced immune activity function caused by the structural changes in the immunogenic protein corona that is coated on the surface of a nanoparticle, and a method for preparing the same. However, these challenges are for illustrative purposes, and the scope of the present disclosure is not limited thereto.

In accordance with an exemplary embodiment, a composite nanoparticle is provided in which an immunogenic plasma protein is coated on the surface of a nanoparticle.

In accordance with another exemplary embodiment, an immunoactivating agents comprising the composite nanoparticle as an active ingredient.

In accordance with yet another exemplary embodiment, a drug delivery system comprising the composite nanoparticle as an active ingredient.

In accordance with still another exemplary embodiment, a cancer treatment agent comprising the composite nanoparticle coupled with an anticancer agent as an active ingredient.

In accordance with yet still another exemplary embodiment, a method for treating cancer in a subject suffering from cancer comprising administering therapeutically effective amount of the cancer treatment agent to the subject.

BRIEF DESCRIPTION OF THE DRAWINGS

Exemplary embodiments can be understood in more detail from the following description taken in conjunction with the accompanying drawings, in which.

DETAILED DESCRIPTION OF EMBODIMENTS

Figure 1A:
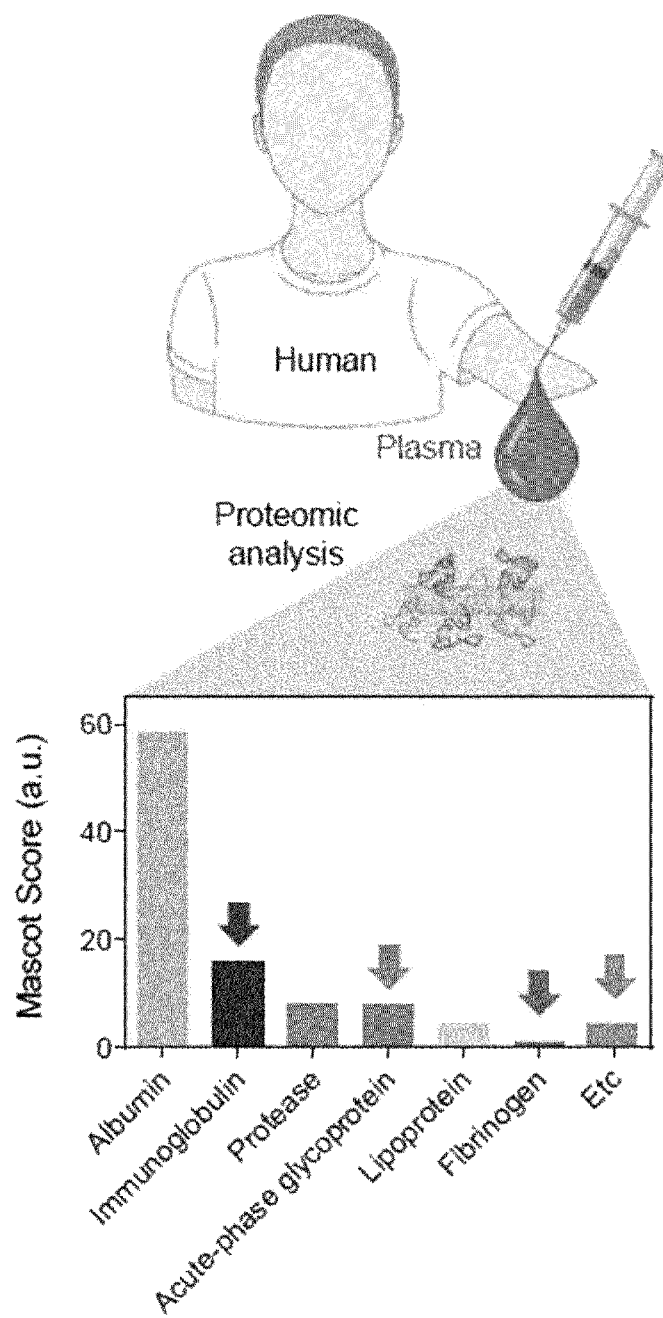
FIG. 1A shows the interaction between human and mouse plasma proteins with CNTs through proteomics analysis, in which shows a diagram illustrating an interaction between human plasma and CNTs.

Hereinafter, specific embodiments will be described in detail with reference to the accompanying drawings.

DEFINITION OF TERMS

As used herein, the term "immunogenic plasma protein" refers to a protein, among plasma proteins present in the blood, which induces an immune response in the body of a subject when exogenously delivered to the subject. There are various types of plasma proteins (e.g., albumin) in plasma, where some of these plasma proteins do not cause any immune response even if they are exogenously injected into a subject, whereas some are known to induce an immune response in the subject. However, the exact cause as to what causes these proteins to have immunogenicity has not been identified.

As used herein, the term "protein corona" refers to a phenomenon in which when nanoparticles are introduced into the blood stream, they are introduced from the human body and proteins are adsorbed to these nanoparticles. Protein corona interferes with the interactions between target ligands on nanoparticles and the binding sites around a cell. Protein corona can be schematically represented as a double-layered coating surrounding nanoparticles. While protein corona consists of a tightly-bound monolayer called a "hard" corona that usually consists of proteins with high affinity around nanoparticles, the outer layer (called the "soft" corona) consists mainly of a loose protein layer that reflects the abundance of serum proteins, including albumin and a derivative thereof (Casals et al., *ACS Nano*. July 27; 4 (7): 3623-32. 2010).

As used herein, the term "pegylation" refers to a process of covalently and non-covalently binding or fusing polyethylene glycol (PEG) polymer chains into molecules and macrostructures (e.g., drugs, therapeutic proteins, and vesicles).

As used herein, the term "unordered structure" was conventionally called an irregular structure in the past by referring to collective states of not having regular repeating structures (e.g., α-helical or β-pleated sheet structures among secondary structures of proteins). Currently, due to the progress in structural analysis, it means those which include parts that show a regular structure like a β-turn. It is conceptually different from an irregular coil in that it has a spatially constant structure, but they are frequently used interchangeably.

DETAILED DESCRIPTION OF INVENTION

According to one aspect of the present disclosure, there is provided a composite nanoparticle in which an immunogenic plasma protein is coated on the surface of a nanoparticle.

In the composite nanoparticle, the immunogenic plasma protein may be α1 acid glycoprotein (AGP), immunoglobulin G (IgG), serum amyloid A, immunoglobulin E (IgE), or alpha 1-lipoprotein, and the nanoparticle may be a PEG-coated nanoparticle in which polyethylene glycol (PEG) is coated on the surface thereof.

In the composite nanoparticle, the immunogenic plasma protein may have an increased irregular structure (unordered structure) by the PEG, and the nanoparticle may be a gold nanoparticle or carbon nanotube.

In the composite nanoparticle, the carbon nanotube may be a single-walled carbon nanotube, a multi-walled carbon nanotube, or a multi-expressed carbon nanotube. The carbon nanotube may have a diameter of 5 nm to 40 nm, and the carbon nanotube may have a length of 100 nm to 300 nm.

According to another aspect of the present disclosure, there is provided an Immunoactivity agents containing the composite nanoparticle as an active ingredient.

According to still another aspect of the present disclosure, a drug delivery system containing the composite nanoparticle as an active ingredient is provided.

According to still another aspect of the present disclosure, there is provided a cancer treatment agent in which an anticancer agent is bound to the drug delivery system.

In the cancer treatment agent, the cancer may be selected from the group consisting of liver cancer, colorectal cancer, uterine cervical cancer, kidney cancer, stomach cancer, prostate cancer, breast cancer, brain tumor, lung cancer, uterine cancer, colon cancer, bladder cancer, blood cancer, and pancreatic cancer. The anticancer agent may be doxorubicin, epirubicin, adriamycin, cis-platin, mitomycin-C, or daunomycin.

According to still another aspect of the present disclosure, there is provided a method for treating cancer, which includes administering the cancer treatment agent to a subject having cancer.

Previous studies have analyzed quantitative proteomics data of plasma protein corona that interacts with NPs, and the physicochemical properties (especially the size) of NPs have been found to be an influencing factor in determining a higher affinity for plasma proteins (M. P. Monopoli, et al., *J Am Chem Soc*, 133, 2525. 2011). In addition, complement activation was considered to have a potential danger due to changes in the protein corona (Y. Yan, et al., *ACS Nano*, 7, 10960. 2013). Plasma protein coating around NPs can affect their uptake levels, thereby making it possible for them to avoid the engulfment and elimination processes performed by immune cells. In particular, coating of NPs with serum proteins (e.g., bovine serum fibrinogen (BFG), gamma globulin (Ig), transferring (TF) and bovine serum albumin (BSA)) resulted in lower cytotoxicity compared to uncoated NPs in several cell lines (V. H. Nguyen, et al., *Int J Nanomedicine*, 12, 3137. 2017). In particular, the structural variations in the plasma protein corona due to its interaction with NPs was considered "another cause" to activate the subsequent inflammatory response, and previous studies have reported that pro-inflammatory signaling pathways are initiated by the binding of particular plasma proteins to NPs (Z. J. Deng, et al., *Nat Nanotechnol*, 6, 39. 2011). However, the mechanism relating to the structural variations in plasma proteins in the in vivo immune response has not yet been identified. As such, demonstration of immune responses in an in vivo model will elucidate how structural variations in the protein corona can affect immune responses in specific immune organs, such as lymph nodes and spleen. In the present disclosure, it was clearly demonstrated that human and mouse plasma proteins interact with carbon nanotubes (CNTs) and the mascot score is more important for the immunogenic coronas interacting with CNTs than non-immunogenic coronas. While the immunogenic proteins α1 acidglycoprotein (AGP, acute-phase plasma protein for inflammation) and immunoglobulin G (IgG, the most common antibody secreted by B cells and found in blood and extracellular fluid) were bound to CNTs, and in order to examine positive or negative immune responses according to the type of formation of protein corona surrounding the CNTs (i.e., immunogenic or non-immunogenic) fibrinogen (FN, a glycoprotein that helps blood clot formation) and vitronectin (VN, a glycoprotein involved in tissue cell adhesion and proliferation) were bound to CNTs.

Figure 11:
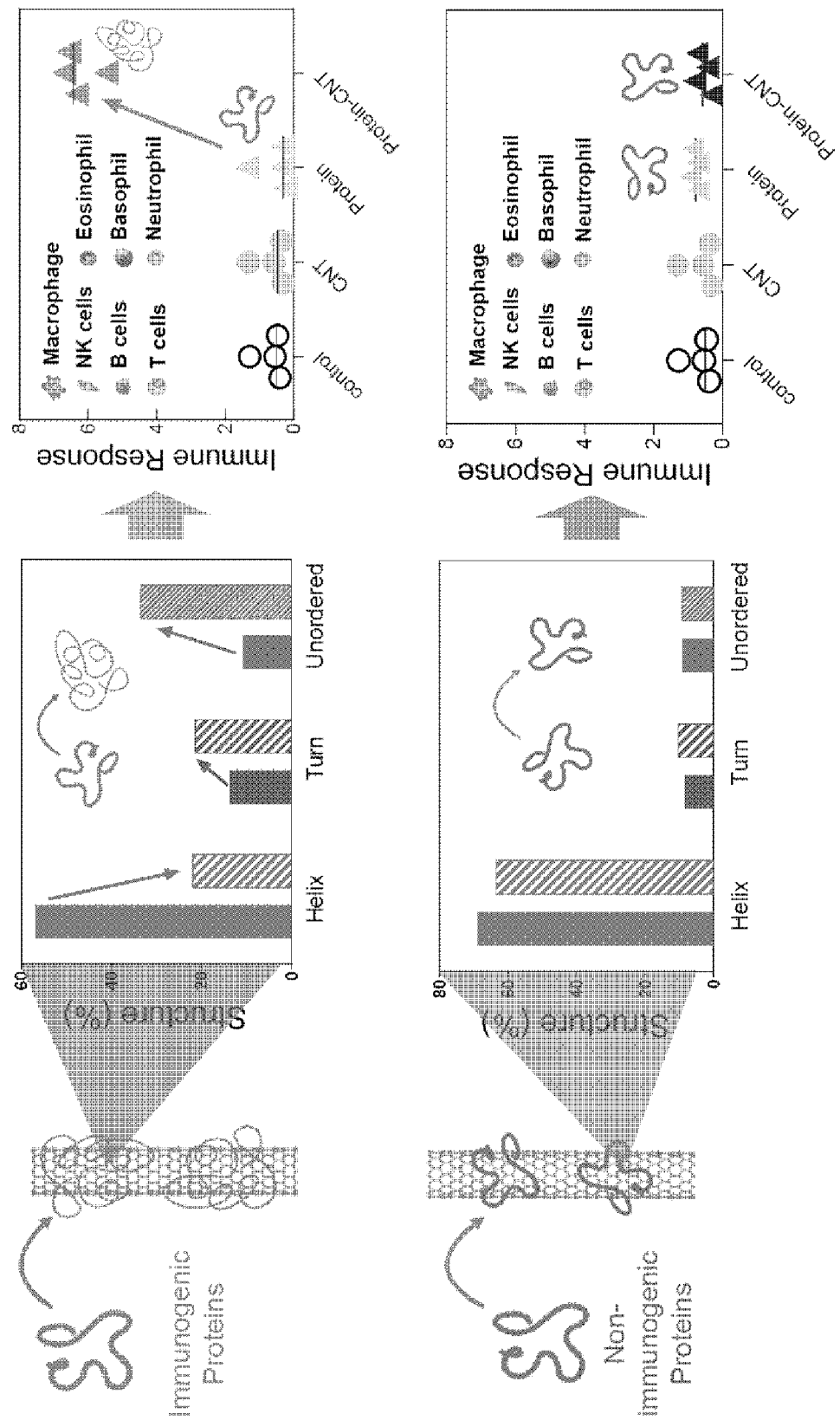
FIG. 11 shows schematic diagrams schematically illustrating that the structural changes in the immunogenic proteins surrounding CNTs of the present disclosure induces an innate immune response.

In general, when nanoparticles are injected into the bloodstream through a vein, they interact with various biomolecules in plasma, and thus, the immunotoxic response of the nanoparticles directly depends on the type of the protein corona formed around the nanoparticles. The present inventors have confirmed that in corona while the structures of the immunogenic proteins are greatly affected by the nanotube, the structures of the non-immunogenic proteins are slightly modified. Importantly, while structural changes in the immunogenic protein corona increase the level of reactive oxygen species (ROS) and secrete pro-inflammatory cytokines by macrophages, mild structural changes in the non-immunogenic protein corona did not induce ROS production or secrete proinflammatory cytokines. In addition, in-vivo analysis confirmed that the immune response stimulated by the immunogenic protein corona caused a significant increase in innate immunity in the spleen, but the non-immunogenic protein did not induce any subsequent immune response in the spleen. Conclusively, the present inventors have found that the greatly unfolded structures of the immunogenic corona have a significant correlation with the subsequent activation of proinflammatory and innate immune responses. That is, they have confirmed that the form of the immunogenic corona was easily modified unlike the form of the non-immunogenic corona and have confirmed that the structural changes in the immune-induced corona around CNTs significantly induced proinflammatory responses in vitro and in vivo (FIG. 11).

Hereinafter, the present disclosure will be described in more detail through Examples. However, the present disclosure is not limited to the Examples disclosed herein but may be implemented in various different forms. The following Examples are provided to make the disclosure of the present disclosure complete, and to fully inform those of ordinary skill in the scope of the invention.

Example 1: Preparation of Human and Mouse Plasma

Human plasma samples used in the present disclosure were obtained from five healthy individuals in accordance with the approval of the Institutional Review Boards in Korea. The blood was collected from each donor in the presence of heparin and centrifuged at 800×g for 5 minutes to pellet blood cells. Then, the supernatant (plasma) was collected and stored as aliquots at −70° C. In addition, six-week-old male ICR mice were purchased from DBL Co., Ltd. (Daejeon, Korea) and housed five mice per cage in laminar air flow (LAF). During the experiment, the conditions of a temperature of 22±2° C. and a relative humidity of 55±5% were maintained. The care and treatment of the mice were performed in accordance with the guidelines of the Public Health Service Policy on the Care and Use of Laboratory Animals, and they were approved by the Institutional Animal Care and Use Committee. In addition, the mice were euthanized with carbon dioxide for sample collection, whole blood was collected from the celiac artery in a heparin-coated tube, thrombus was removed for plasma collection, and the supernatant was centrifuged at 800×g at 4° C. for 5 minutes. Thereafter, the plasma was then stored at −70° C. until further analysis.

Example 2: Culture of Plasma and Nanotubes

For culturing plasma and nanotubes, CNTs in PBS (1 mg/mL) were incubated with 10% plasma at 37° C. for one hour. Thereafter, unbound proteins were separated from the CNTs under conditions of centrifugation at 50,000×g at 4° C. for 40 minutes, and plasma without CNTs was used as a control to prevent precipitation of the proteins. After the centrifugation, the pellet was carefully washed twice with PBS, resuspended in a sample buffer (125 mM Tris-HCl, 10% SDS, 20% glycerol, 1% β-mercaptoethanol, and 0.5% bromophenol blue) and heated at 95° C. for 5 minutes to detach the particle-bound proteins.

Example 3: Proteome Analysis by 2D-LC-MS/MS

The gel bed was cut into small pieces according to a conventional method and proteolytic digestion was performed with proteolytic-grade trypsin (Qiagen) (Y. E. Cho, et al., Baek, *Mol Cell* Proteomics, 11, M111 010884. 2012). Then, the trypsin peptide was extracted from the gel using continuous extraction. For the 2D-LC method, nanoscale LC separation of the trypsin peptide mixture (1 μg of peptide) was performed with the nanoACQUITY system (Waters Corporation, Milford, MA, USA) using a hybrid silica-based XTerra MS C18 column (5 mm, 100 mm×300 μm) as a one-dimensional column and a BEH C18 analytical reversed-phase column (1.7 μm, 25 cm×75 μm) as a two-dimensional column (Waters Corporation) according to a conventional method (Y. E. Cho, et al., Baek, *Proteomics*, 13, 1257. 2013). Then, the sample was initially transferred to a one-dimensional column with 0.1% aqueous formic acid solution at a flow rate of 0.5 μL/min for 5 minutes. In particular, mobile phase A consisted of 20 mM ammonium formate and mobile phase B consisted of 20 mM ammonium formate/CAN (pH 10.0) for a one-dimensional column. Thereafter, for protein identification, the raw data files from MS/MS were converted into a peak list using Mascot Distiller (Matrix Science, version 2.3.2) with default parameters.

Example 4: Experimental Materials

Purified CNTs with an outer diameter of less than 10 nm (CNT10, 900-1255, SES, USA) and 30 nm (CNT30, 900-1260, SES, USA) were purchased from a vendor and oxidized according to a conventional method (Y. K. Lee, et al., Khang, *ACS Nano*, 7, 8484. 2013). Amino-propyl PEG (PEG, MW=5 kDa, NOF Corp., Japan) was used as PEG-coated CNTs, whereas α1 acid-glycoprotein (AGP), immunoglobulin G (IgG), fibrinogen (FN), and vitronectin (VN) were purchased from Sigma-Aldrich (G9885, 14506, F4883, A9511, and 5051). Proteins were non-covalently bound and PEGylated to CNTs through various interactions (i.e., T-T, polar-π, electrostatic interactions, and van der Waals forces). Plasma protein-CNTs (i.e., AGP-CNT, IgG-CNT, FN-CNT, and VN-CNT) binding was used to examine immunotoxicity based on the extent of structural changes in the protein corona depending on the type of the plasma protein surrounding the CNTs.

Example 5: Protein Binding and Physical Characterization

Carboxylated CNTs were dispersed in distilled deionized water (DW) by sonication (Jeio Tech. Co., Daejeon, Korea) for 5 minutes. The sufficiently dispersed CNTs were washed three times by centrifugation using a filter tube (Amicon YM-50, 100 kDa, Millipore), and for PEGylation of CNTs, PEG (25 mg/mL) was added to a CNT solution (5 mg/mL) and the mixture was sonicated at 4° C. for 30 minutes. Thereafter, centrifugation was performed at 4,000 rpm for 10 minutes. Then, the PEGylated CNT solution, before binding to the protein, was washed with 2-morpholinoethanesulfonic acid (MES) buffer (50 mM, pH 8.0, M3671, Sigma) at least three times. The selected plasma proteins (i.e., AGP, IgG, FN, and VN) were prepared at a concentration of 1 mg/mL in the same MES buffer and were added to the PEGylated CNT solution for binding. Then, the mixture was incubated with shaking at 4° C. for 48 hours and the immune corona of the CNTs PEGylated in the MES buffer (i.e., AGP-CNT, IgG-CNT, FN-CNT, and VN-CNT) were filtered three or more times (Amicon YM-50, 100 kDa, Millipore), and centrifugation was performed at 4,000 rpm to remove unbound proteins. After the completion of the binding process, the plasma protein corona-CNT (i.e., AGP-CNT, IgG-CNT, FN-CNT, and VN-CNT) complex was maintained in PBS (pH 7.2) until the physical properties thereof were confirmed. After drying the sample in a vacuum oven at 60° C. for at least two days, the percentage of proteins bound to CNTs was calculated by measuring the changes in weight between completely-dried CNTs and dried plasma protein-CNTs on a PTFE membrane (JGWP04700, Omnipore). In addition, the diameter and zeta potential of the complex in PBS (pH 7.2) were measured using dynamic light scattering (DLS) and electrophoretic light scattering (ELS, Zetasizer Nano, Malvern, UK).

Example 6: Circular Dichroism Spectroscopy

The circular dichroism (CD) spectrum was analyzed with a Chirascan CD spectrometer (Applied Photophysics, Randalls, UK), and the data were collected at room temperature in the wavelength range of 190 nm to 260 nm using a 1 nm quartz cuvette (300 μL). Then, samples were prepared in sodium phosphate buffer (pH 7.4, 25 mM) at a concentration of 0.2 mg/mL, spectrum data were collected at 1-nm bandwidth, 0.5 s per point, and each spectrum was acquired from five cumulated ones (average). Additionally, the content of the secondary structure from the CD spectrum was analyzed by a CDPro software using the CDSSTR algorithm.

Example 7: Cell Culture and Viability Assay

The BALB/c macrophage cell line J774A.1 was obtained from the American Type Culture Collection (ATCC, TIB-67, Manassas, VA, USA), and the cells were cultured in Dulbecco's modified Eagle medium (DMEM, Gibco, 11995-065, Waltham, MA, USA), non-heat-treated inactivated 10% fetal bovine serum (FBS, Gibco, 16000-044) and 1% penicillin/streptomycin (Gibco, 10378016) were added thereto at 37° C. and 5% $CO_2$ conditions. In addition, the human monocyte cell line THP-1 was purchased from the American Type Culture Collection (ATCC, TIB-202, Manassas, VA, USA), and the cells were cultured in RPMI 1640 medium (Gibco, 11875-093), and the non-heat-treated inactivated 10% fetal bovine serum (FBS, Gibco, 16000-044) and 1% penicillin/streptomycin (Gibco, 10378016) were added at 37° C. and 5% $CO_2$ conditions. Then, the cells ($5 \times 10^3$ cells/well in a 96-well plate) were treated with serum proteins (i.e., IgG, AGP, FNG, and VN), PEGylated CNTs, and plasma protein-CNTs (i.e., IgG-CNT, AGP-CNT, FN-CNT, and VN-CNT) at various concentrations for 24 hours. Cell viability assay was performed using 3-(4,5-dimethylthiazol-2yl) 2,5-diphenyl tetrazolium bromide (MTT, Amresco, Solon, OH, USA), and MTT (1 mg/mL) was added to each well containing the sample 24 hours after the treatment, and the mixture was incubated for two additional hours. In addition, DMSO was added to dissolve formazan crystals, and the absorbance of each sample was measured by comparing it with that of the control, and then expressed as a percentage.

Example 8: Detection of Intracellular Reactive Oxygen Species (ROS)

The production of reactive oxygen species (ROS) was measured by detecting the fluorescence intensity of an oxidizer-sensitive probe. J774A.1 and THP-1 cells ($5 \times 10^3$ cells/well in a 96-well plate) were treated with serum proteins (i.e., IgG, AGP, FN, and VN), PEGylated CNTs, and plasma protein-CNTs (i.e., IgG-CNT, AGP-CNT, FN-CNT, and VN-CNT) at various concentrations for two hours and stimulated with LPS (50 ng/mL, L5293, Sigma) for hours. These cells were added to a PBS solution containing 10 μM of 2', 7'-dichlorodihydrofluorescein diacetate (DCF-DA, D6883, Sigma), and the intracellular and extracellular dye concentrations were equilibrated at 37° C. and 5% $CO_2$ conditions for 30 minutes. In addition, the changes in fluorescence intensity of DCF-DA were recorded with excitation at 480 nm and emission at 525 nm by a Victor X3 multi-label plate reader (Perkin Elmer, USA).

Example 9: RT-PCR

In order to measure the expression of cytokines, quantitative real-time PCR (CFX 96, Bio-Rad, Hercules, CA, USA) was performed in accordance with the manufacturer's instructions, and J774A.1 was pretreated with immune-inducing proteins (IgG and AGP), PEGylated CNTs, and immune-induced protein-CNT complexes (IgG-CNTs and AGP-CNTs) for two hours followed stimulation with LPS (50 ng/mL) for 12 hours. In addition, total RNA was isolated from cells and the spleen using the QIAzol lysis reagent (#79306, Qiagen, Hilden, Germany) and the isolate was purified by RNeasy Mini Kit (#74104, Qiagen). Then, RNA (500 ng) was treated with DNase I (New England Biolabs, Ipswich, MA, USA) and cDNA was synthesized using the iScript cDNA Synthesis Kit (Bio-Rad, Hercules, CA, USA). In particular, reverse transcription was performed under the following conditions: at 45° C. for 60 minutes and at 95° C. for 5 minutes. Then, 2 μL of cDNA (500 ng/ml), 1 μL of a sense and antisense primer solution (0.4 μM), 12.5 μL of iQ SYBR Green supermix (170-8880, Bio-Rad), and 9.5 μL of $dH_2O$ were mixed in each reaction tube to obtain 25 μL of a final reaction mixture. Cycle threshold (Ct) values were calculated using the CFX96 real-time PCR detection system (Bio-Rad) software, and the comparative Ct method (a 2 ΔCt model) was used to calculate the relative fold-change in gene expression being normalized to the averaged GAPDH expression. Sequence information for the primers used for the PCR amplification is summarized in Tables 1 and 2 below.

TABLE 1

Nucleotide sequences of primers of real-time PCR (in-vitro)

| Primer | Nucleotide Sequence (5'-->3') | SEQ ID NO |
|---|---|---|
| Il6 F | ATC TTC TCC TGG GGG TAC TG | 1 |
| Il6 R | CTT TTT CTG CAG GAA CTG GA | 2 |
| Tnf F | CCT ACC AGA CCA AGG TCA AC | 3 |
| Tnf R | AGG GGG TAA TAAAGG GAT TG | 4 |
| Il1b F | CCA GCT GTA GAG TGG GCT TA | 5 |
| Il1b R | GGA TAT GGA GCA ACA AGT GG | 6 |
| GAPDH F | GTA TGA CAA CGA ATT TGG CTA CAG | 7 |
| GAPDH R | TCT CTC TCT TCC TCT TGT GCT CTT | 8 |
| Il6 F | TAG TCC TTC CTA CCC CAA TTT CC | 9 |
| Il6 R | TGG TCC TTA GCC ACT CCT TC | 10 |
| Tnf F | CCT GTA GCC CAC GTC GTA G | 11 |
| Tnf R | GGG AGT AGA CAA GGT ACA ACC C | 12 |
| Il1b F | GCA ACT GTT CCT GAA CTC AAC T | 13 |
| Il1b R | ATC TTT TGG GGT CCG TCA ACT | 14 |
| Il14 F | CTG TAG GGC TTC CAA GGT GCT TCG | 15 |
| Il14 R | CCA TTT GCA TGA TGC TCT TTA GGC | 16 |
| Il13 F | CCT GGC TCT TGC TTG CCT T | 17 |
| Il13 R | GGT CTT GTG TGA TGT TGC TCA | 18 |
| Infg F | ATG AAC GCT ACA CAC TGC ATC | 19 |
| Infg R | CCA TCC TTT TGC CAG TTC CTC | 20 |
| GAPDH F | CTG GTA TGA CAA TGA ATA CG | 21 |
| GAPDH R | GCA GCG AAC TTT ATT GAT GG | 22 |

Example 10: Pro-Inflammatory Cytokines (In-Vivo Model)

The secretion level of proinflammatory cytokines from the spleen was analyzed according to one embodiment of the present disclosure. BALB/c mice (female, 4 to 6 weeks old, and 16 g to 20 g) were purchased from Orient Bio (Seoul, Korea) and housed in a kennel with temperature and humidity control and free from specific pathogens, and they were acclimatized to a 12-hour light-dark cycle (lit at 6:30 AM) for 7 to 14 days until the experiment. All of the animal experiments were performed in accordance with the guidelines for care and use of laboratory animals of Gachon University. For the analysis, CNT-bound immunogenic proteins (i.e., IgG-CNT and AGP-CNT), non-immunogenic proteins (FN-CNT), and free proteins (i.e., IgG, AGP, and FN) in physiological saline at a protein concentration of 5 mg/kg was intravenously injected into female BALB/c mice. CNT-bound plasma proteins and CNT-unbound plasma proteins were injected twice every three days for a week. All of the experimental animals were sacrificed two days after the protein injection.

Example 11: Flow Cytometry

In order to characterize the surrounding phenotypes of splenocytes, splenocytes were isolated according to a conventional method (E. H. Lee, et al., *Ethnopharmacol*, 146, 608. 2013). For this purpose, the spleen isolated from mice was gently pulverized, filtered through a nylon mesh to remove debris thereof, and treated with ammonium chloride-potassium lysis buffer to lyse red blood cells. The isolated splenocytes were resuspended in FACS buffer (PBS containing 10% FCS, 20 mM HEPES and 10 mM EDTA). Then, after blocking Fc receptors with anti-mouse CD16/CD32 (2.4G2, BD Biosciences, San Diego, CA, USA) at 4° C. for 15 minutes, the cells were stained with an antibody at 4° C. for 30 minutes. In particular, the mAbs, Gr-1 (RB6-8C5), F4/80 (BM8), CD3 (145-2C11), and B220 (RA3-6B2) against CD11b (M1/70) were purchased from R&D Systems (Minneapolis, MN, USA); anti-SiglecF (E50-2440) from BD Biosciences; and anti-CD4 (RM4-5) and anti-CD8a (53-6.7) from eBioscience (San Diego, CA, USA). Each sample was analyzed with a FACSCalibur (BD Biosciences) and data was processed using FlowJo software (Tree Star, Ashland, OR, USA).

Example 12: Gel Electrophoresis by SDS-PAGE

For electrophoresis, samples were loaded into a 8% sodium dodecyl sulfate polyacrylamide gel, separated using Bio-Rad at 100 V for 60 minutes, and protein bands were stained with Coomassie blue.

Experimental Example 1: Interaction Between CNTs and Human or Mouse Plasma Proteins For the examination of the major species of plasma proteins (both human and mouse) that interact with CNTs, it is essential to perform pre-screening before allowing certain types of immunogenic (or non-immunogenic) plasma proteins to bind to CNTs. Accordingly, the present inventors incubated 10% plasma with CNTs (30 nm in diameter) for one hour and then the bound plasma proteins were examined by proteomic analysis. In the present disclosure, a mascot score (a total score of interacting proteins) was used as a standard to confirm the formation of hard corona around CNTs.

Figure 1B:
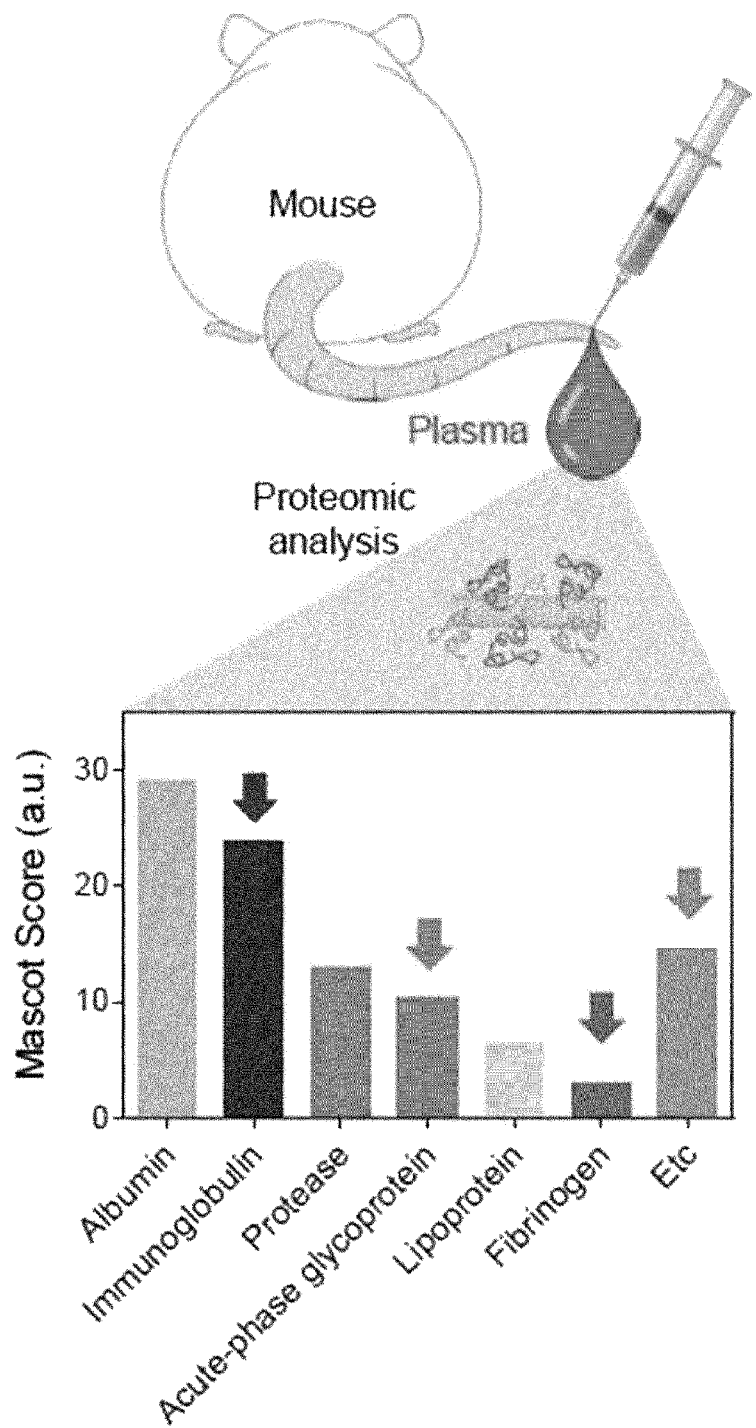
FIG. 1B shows the interaction between human and mouse plasma proteins with CNTs through proteomics analysis, in which shows a diagram illustrating an interaction between mouse plasma and CNTs.

As a result, humans and mice showed the same trend of the mascot score with regard to the plasma proteins bound to CNTs. Overall, it was found that albumin, immunoglobulins, and acute-phase glycoproteins were the major plasma proteins that interacted actively with CNTs. In particular, immunogenic coronas consisting of AGP and IgG showed higher mascot scores than non-immunogenic coronas, such as FN (fibrinogen) and others (including VN) (FIGS. 1A and 1B). Based on the proteomics analysis, the hard corona surrounding CNTs was mostly consisting of albumin, immunogenic proteins, and non-immunogenic proteins.

Figure 1C:
FIG. 1C shows the interaction between human and mouse plasma proteins with CNTs through proteomics analysis, in which shows a diagram schematically illustrating the morphology of the immunogenic (IgG and AGP) and non-immunogenic (FN and VN) protein corona bound to CNTs.

Experimental Example 2: Binding of Immunogenic and Non-Immunogenic Protein Corona Around CNTs The hard corona surrounding the NP is more stable than the soft corona (P. C. Ke, et al., *ACS Nano*, 4, 3623. 2010). However, in order to obtain a consistent (in vitro and in vivo) immune response induced by certain types of plasma proteins surrounding the NPs, more stable and stronger binding than conventional hard coronas will be required. In this regard, the plasma protein corona artificially formed around the CNT mimics the hard corona and it may be helpful to confirm the selective immune response resulting therefrom. To prepare a stable hard corona surrounding CNTs, immunogenic coronas (both IgG and AGP) and non-immunogenic coronas (FN and VN) were bound to CNTs. In addition, for the comparison of immune responses by the changes in the size of interacting CNTs, PEGylated CNTs having different diameters (10 nm and 30 nm) were bound to immunogenic plasma proteins and non-immunogenic plasma proteins (FIG. 1C).

Figure 2A:
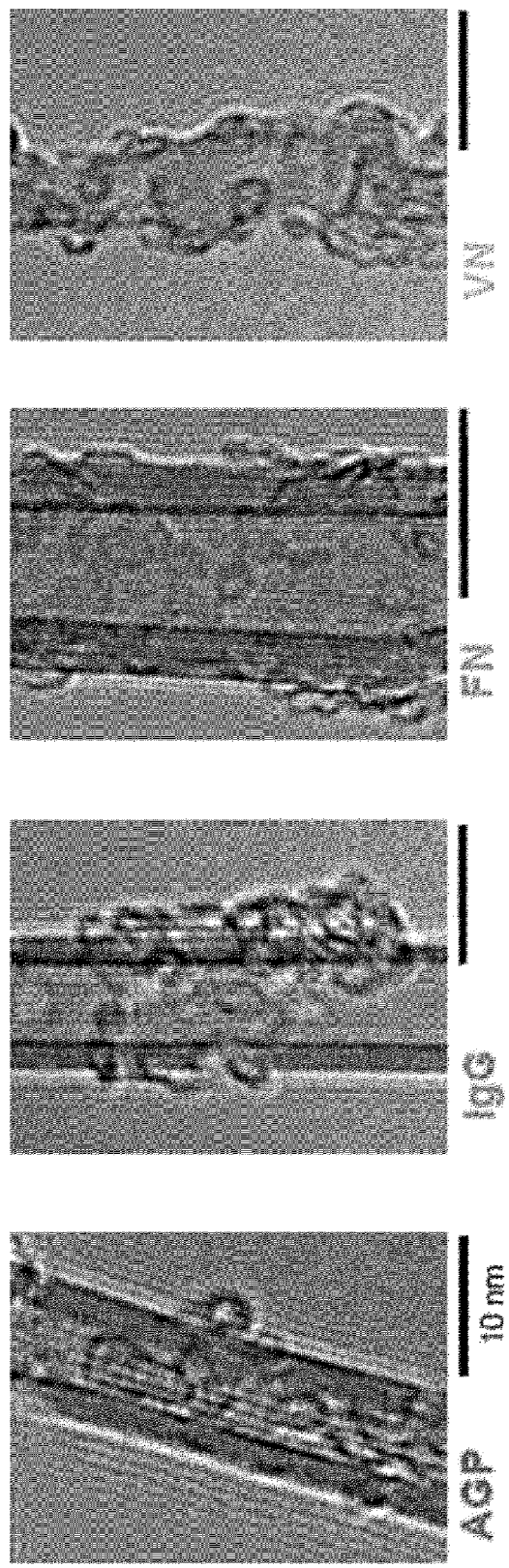
FIG. 2A shows analysis results of physical properties of the plasma protein corona around CNTs, in which shows TEM images of the immunogenic and non-immunogenic protein corona bound to the CNTs (scale bar, 10 nm).
Figure 2B:
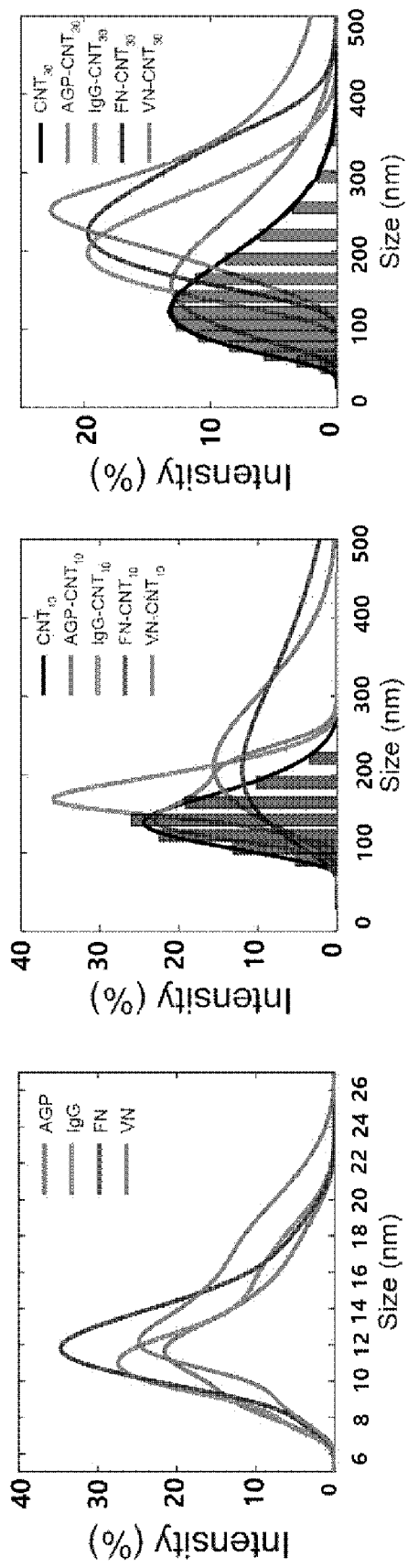
FIG. 2B shows analysis results of physical properties of the plasma protein corona around CNTs, in which shows graphs analyzing the size (length) of the protein, the immunogenic protein corona of CNT10 and the immunogenic corona of CNT30.
Figure 2C:
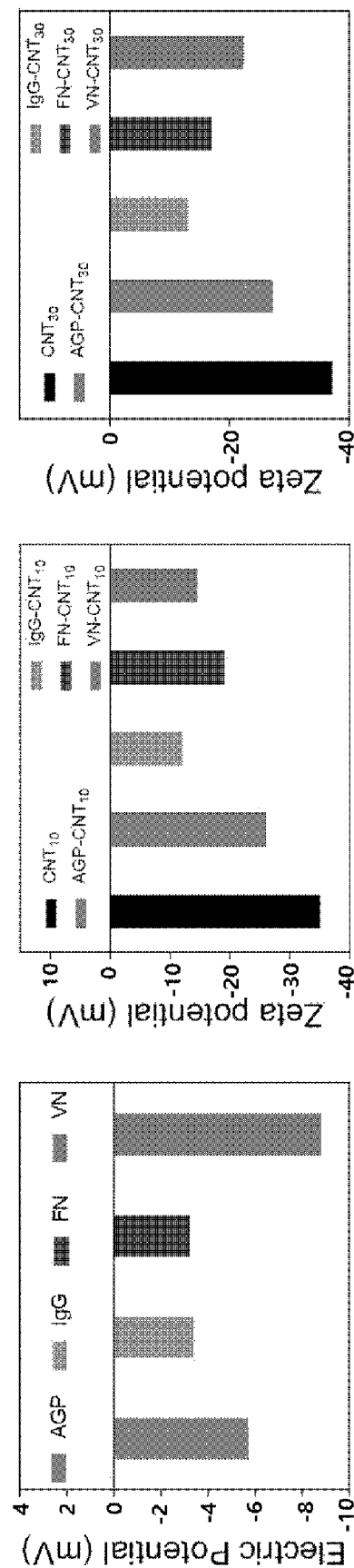
FIG. 2C shows analysis results of physical properties of the plasma protein corona around CNTs, in which shows graphs illustrating analysis results of the negative charges for the proteins and the electric potential of immunogenic and non-immunogenic proteins for CNT10 and CNT30 in PBS (pH 7.2).

As a result, the TEM images clearly showed the plasma protein corona bound around CNTs (FIG. 2A). The hydrodynamic size of plasma proteins and CNT10 (diameter <10 nm) was about 10 nm and 120 nm (average length of CNT10), respectively. After interaction with AGP, IgG, FN, and VN, the length of CNT10 increased to 250 nm (AGP-CNT10), 200 nm (IgG-CNT10), 260 nm (FNCNT10), and 180 nm (VN-CNT10), respectively. In addition, the average length (30 nm in diameter and 140 nm in length) of CNT30 after the interaction with AGP, IgG, FN, and VN was increased to 150 nm (AGP-CNT30), 210 nm (IgG-CNT30), 250 nm (FN-CNT30), and 280 nm (VN-CNT30), respectively (FIG. 2B). The electric potential of each protein was −5.6 mV (AGP), −3.3 mV (IgG), −3.2 mV (FN) and −8.8 mV (VN) (FIG. 2C), and all of the proteins (AGP, IgG, FN and VN) were carrying a weak negative charge due to their isoelectric points (PIS). AGP was 2.7 to 3.5; IgG was 6.9; FN was 5.5; and VN was 5.67 (at pH >PI, the protein carried a net negative charge) (Y. Lee, et al., *J Am Chem Soc*, 129, 5362. 2007). The potentials of CNT10 and CNT30 were −35 mV and −37 mV, respectively, and the potential change after protein corona formation was slightly more positive than that of PEGylated CNTs (FIG. 2C).

Figure 3A:
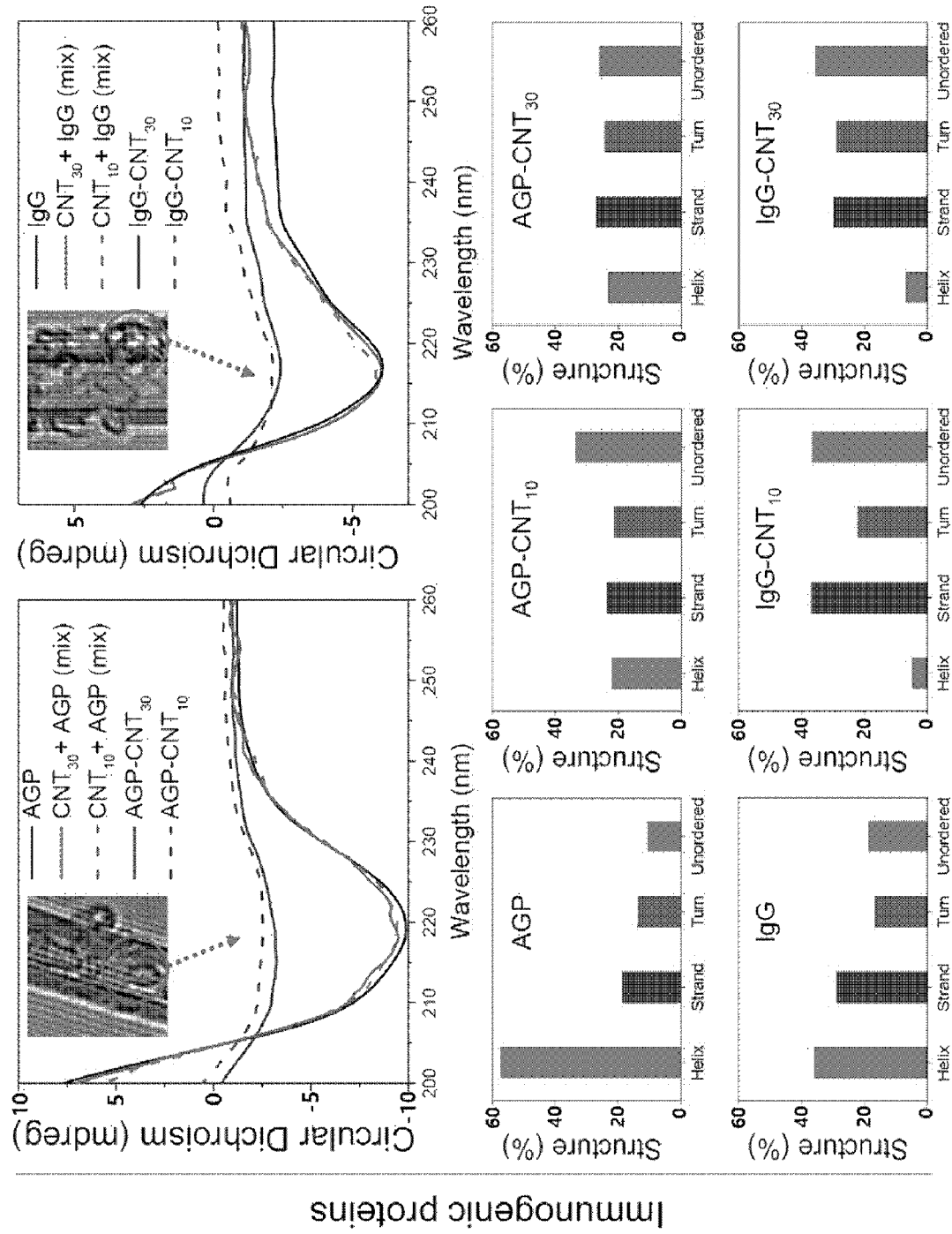
FIG. 3A shows graphs illustrating the analysis results of the CD spectrum of the immunogenic protein corona (AGP and IgG) surrounding CNTs, in which the structural changes in the immunogenic protein corona around the CNTs are analyzed.
Figure 3B:
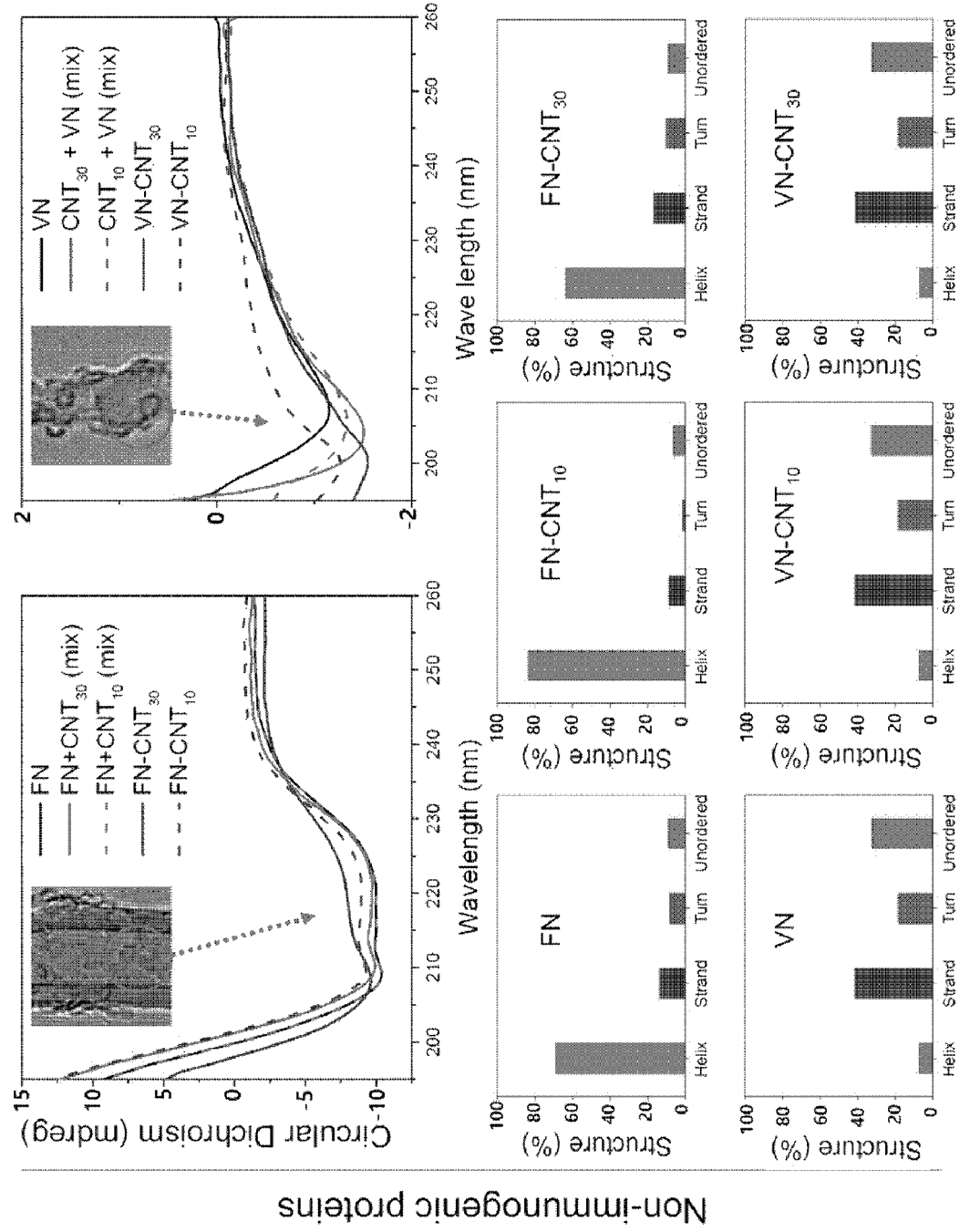
FIG. 3B shows graphs illustrating the analysis results of the CD spectrum of the non-immunogenic protein corona (FN and VN) surrounding CNTs, in which the structural changes in the non-immunogenic protein corona around the CNTs are analyzed.
Figure 4A:
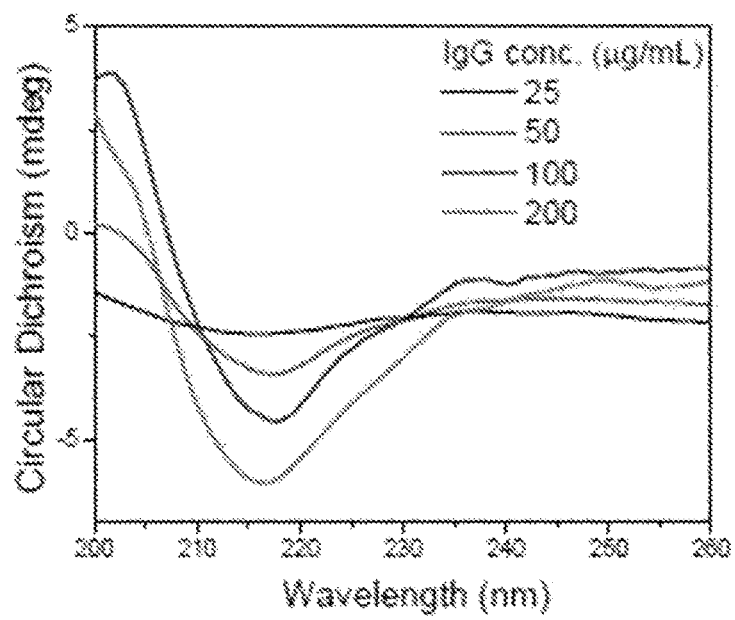
FIG. 4A shows graphs illustrating the analysis results of the changes in circular dichroism spectra of immunogenic IgG proteins according to protein concentration.
Figure 4B:
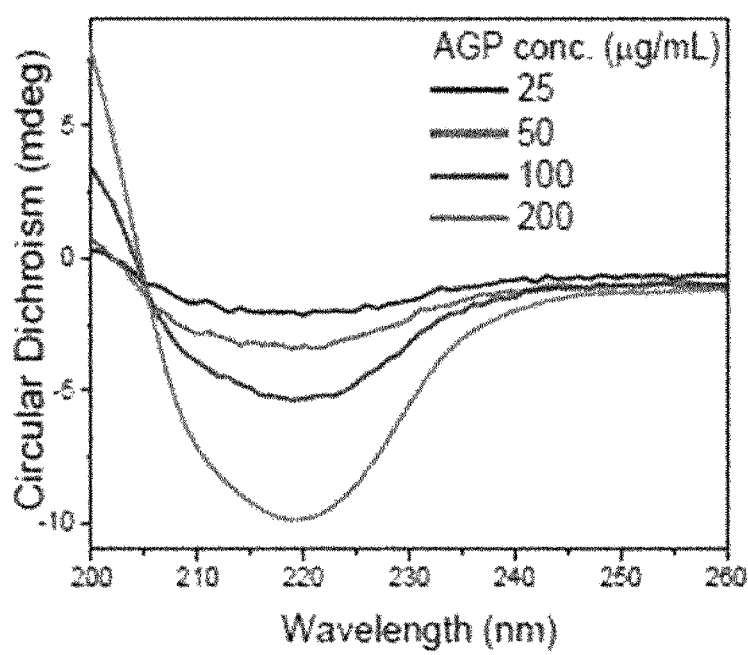
FIG. 4B shows graphs illustrating the analysis results of the changes in circular dichroism spectra of immunogenic AGP proteins according to protein concentration.
Figure 4C:
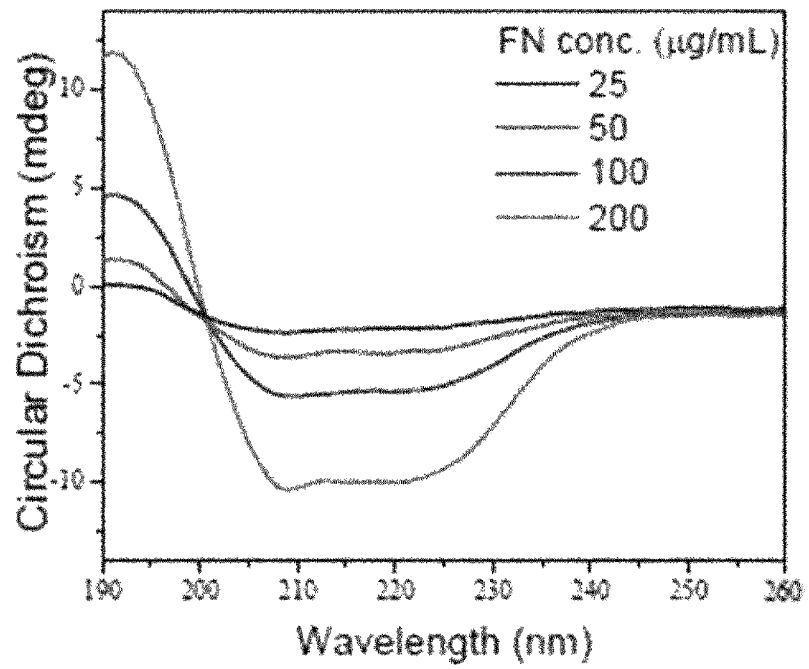
FIG. 4C shows graphs illustrating the analysis results of the changes in circular dichroism spectra of non-immunogenic FN proteins according to protein concentration.
Figure 4D:
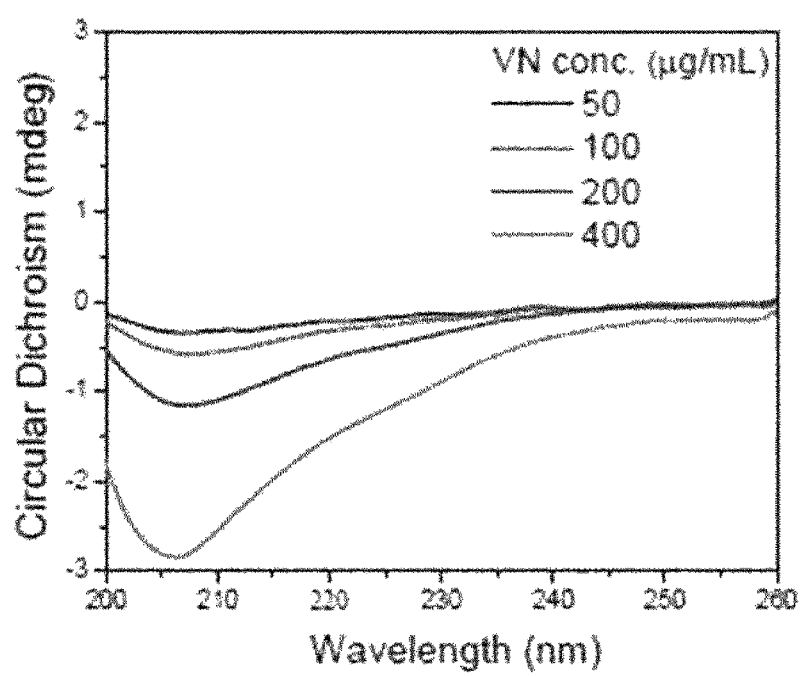
FIG. 4D shows graphs illustrating the analysis results of the changes in circular dichroism spectra of non-immunogenic VN proteins according to protein concentration.

Experimental Example 3: Structural Changes in Immunogenic Protein Corona Around CNTs The secondary structure of the plasma protein corona was analyzed by far-ultraviolet circular dichroism (CD) spectra. As a result, while the secondary structure of immunogenic proteins (AGP and IgG) was significantly affected by CNTs, simple mixing of PEGylated CNTs with immunogenic proteins (AGP and IgG) did not induce a significant change in protein structure (FIGS. 3A, 3B, 4A to 4D). Between the two proteins, the secondary structure of AGP was more affected, and the degree of changes in the secondary structure was slightly increased in CNTs with a smaller diameter (10 nm) than CNTs with a larger diameter (30 nm). The changes in the secondary structure of IgG showed the same trend as in AGP and showed a significant change after its binding to CNTs (a larger change in CNTs with a diameter of 10 nm than CNTs with a diameter of 30 nm) (FIG. 3A). The observation results above are consistent with the results of previous studies, suggesting that CNTs with a smaller diameter induce a larger structural change (X. Zhao, et al., *Hazard Mater*, 292, 98. 2015). In contrast, FN and VN showed minor structural changes in the secondary structure regardless of the size of the interacting CNTs (FIG. 3B). Therefore, the above results clearly suggest that the secondary structural change in corona is induced depending on the type of proteins (immunogenic or non-immunogenic proteins). In addition, in the secondary structure of immunogenic proteins, narrow CNTs induced greater changes than wide CNTs.

The secondary structures of all of the proteins experimented in the present disclosure were further analyzed by the CDSSR method. Specifically, the secondary structure of AGP originally consisted of α-helices (57.08%), β-strands (18.52%), turns (13.71%), and unordered structures (10.71%). After binding with PEGylated CNTs, the α-helix structure of AGP was decreased most significantly from 57.06% to 23.02% in CNT30 and from 57.06% to 21.39% in CNT10. In the case of IgG, the α-helix structure was decreased from 35.19% to 6.63% in the presence of CNT30 and from 35.91% to 4.6% in the presence of CNT10 (FIG. 3A). This suggests that the relative changes in the α-helix structure of AGP and IgG were significantly affected by the interaction with CNT10, and that the unordered structures and the structures of turns replaced the decrease in the α-helix structure (FIG. 3A).

Although CNTs with a slightly larger diameter (CNT30) showed the same trend as the turn and unordered structures increased and the α-helix structure decreased (FIG. 3D), there were no obvious structural changes in FN and VN regardless of the size of the CNTs (both 10 nm and 30 nm) (FIG. 3B). Therefore, the degree of change in the secondary structure of immunogenic plasma proteins was significantly affected by their binding to the CNTs compared to non-immunogenic proteins. In addition, the CNT10 with a small diameter further enhanced the degree of changes in the secondary structure of immunogenic proteins, particularly AGP (FIG. 3A).

Experimental Example 4: Release of Proinflammatory Cytokines by Immunogenic Proteins Around the CNTs In order to confirm whether immunotoxicity is affected by structural changes in corona proteins, the present inventors mixed LPS-induced murine macrophages (J774A.1) and human monocytes (THP-1) with immunogenic coronas (AGP and IgG) surrounding CNTs (both 10 nm and 30 nm). Examination of ROS production by macrophages and monocytes after treatment with immunogenic corona and non-immunogenic corona is a prerequisite before the subsequent analysis of proinflammatory cytokines. Accordingly, the J774A.1 and THP-1 cells were cultured with plasma protein coronas (IgG, AGP, FN, and VN) at various concentrations in CNTs for two hours (after 12 hours of LPS stimulation) and ROS production was measured using DCF-DA (2', 7'-dichlorodihydrofluorescein diacetate) (FIGS. 5A, 6A, 6B, 7A and 7B).

Figure 5A:
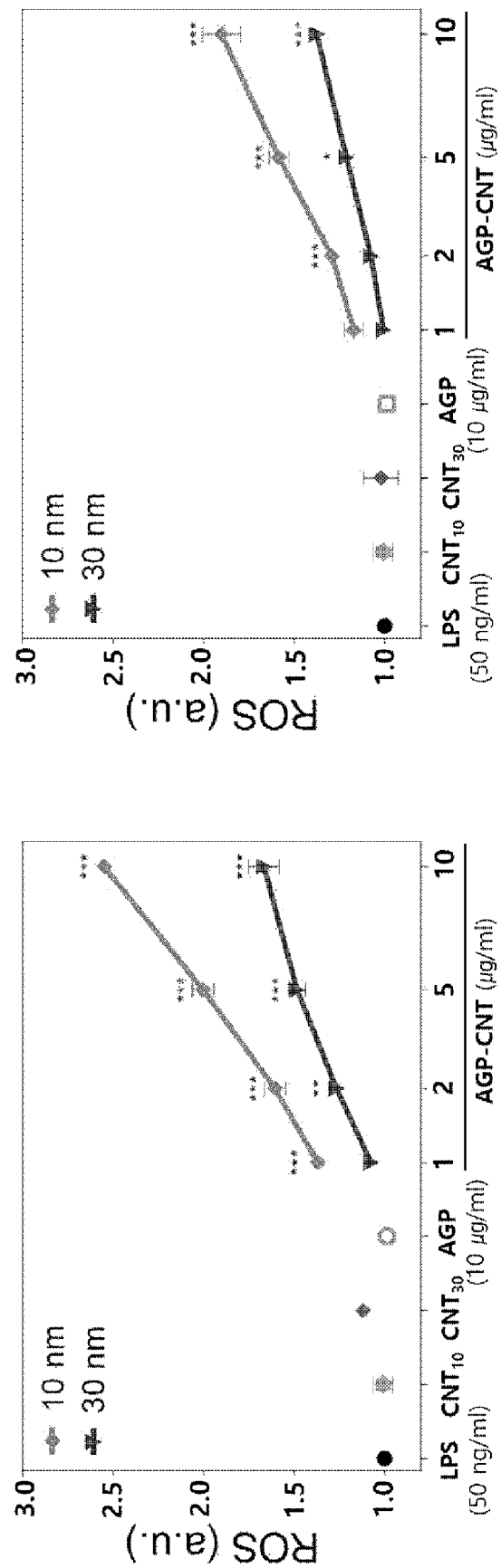
FIG. 5A shows graphs illustrating the analysis results of the secretion of ROS and pro-inflammatory cytokines in macrophages by immunogenic proteins surrounding CNTs, in which shows graphs illustrating the changes in ROS level of J774A.1 cells due to immunogenic protein corona (AGP and IgG) at 10 nm (red) and 30 nm (blue) of CNTs.
Figure 5B:
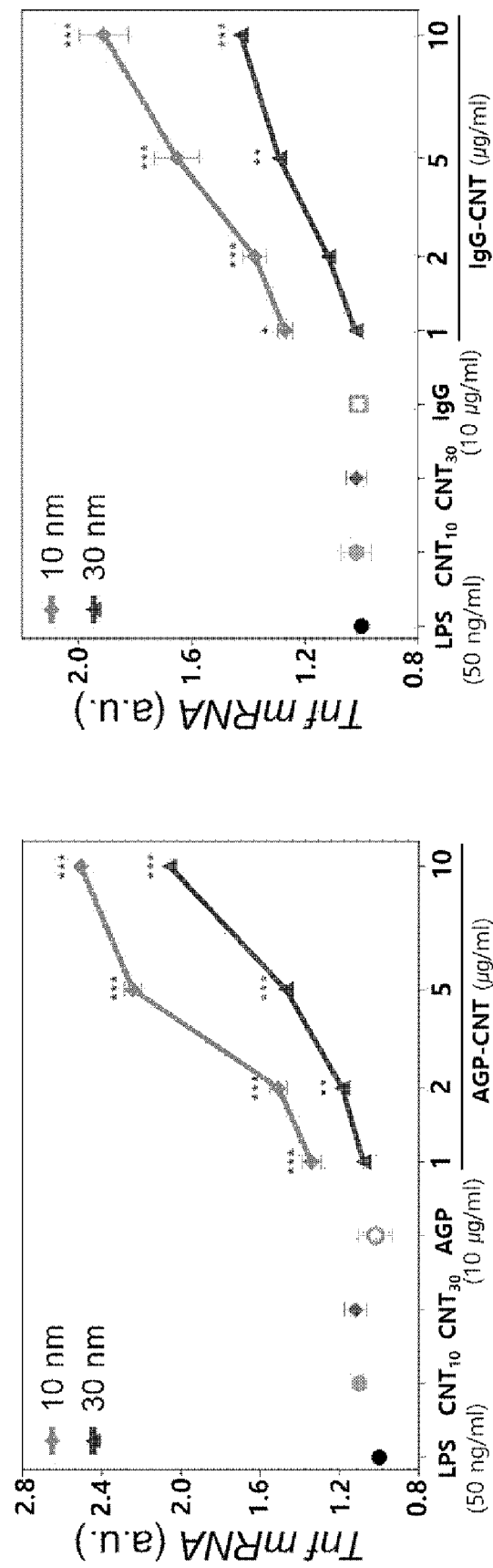
FIG. 5B shows graphs illustrating the analysis results of the secretion of ROS and pro-inflammatory cytokines in macrophages by immunogenic proteins surrounding CNTs, in which shows graphs illustrating the changes in Tnf mRNA level in J774A.1 cells due to immunogenic protein corona (AGP and IgG) at 10 nm (red) and 30 nm (blue) of CNTs.
Figure 5C:
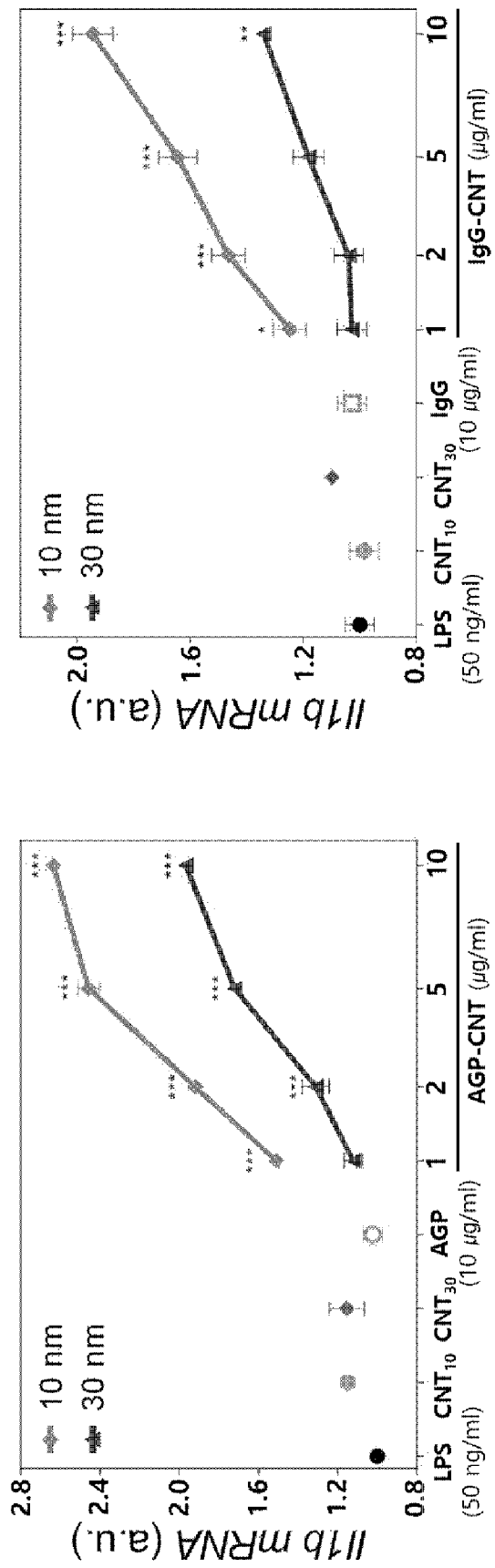
FIG. 5C shows graphs illustrating the analysis results of the secretion of ROS and pro-inflammatory cytokines in macrophages by immunogenic proteins surrounding CNTs, in which shows graphs illustrating the changes in Il1b mRNA level in J774A.1 cells due to immunogenic protein corona (AGP and IgG) at 10 nm (red) and 30 nm (blue) of CNTs.
Figure 5D:
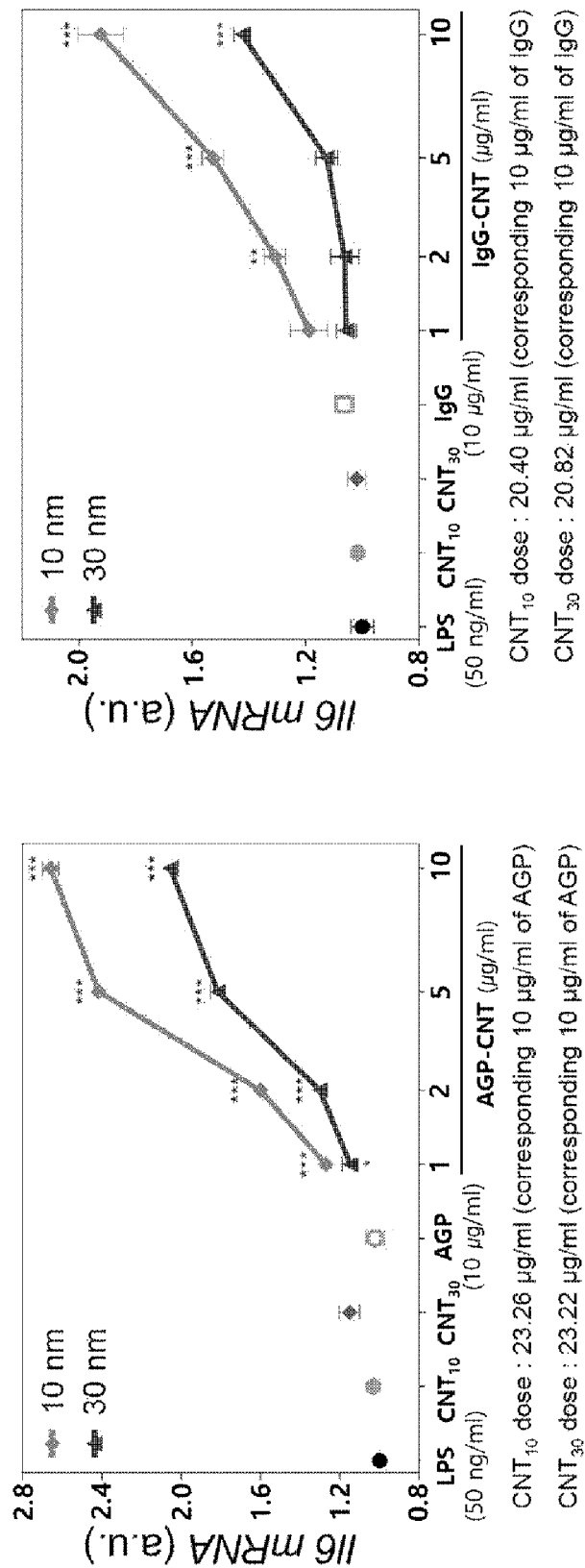
FIG. 5D shows graphs illustrating the analysis results of the secretion of ROS and pro-inflammatory cytokines in macrophages by immunogenic proteins surrounding CNTs, in which shows graphs illustrating the changes in Il6 mRNA level in J774A.1 cells due to immunogenic protein corona (AGP and IgG) at 10 nm (red) and 30 nm (blue) of CNTs.
Figure 6A:
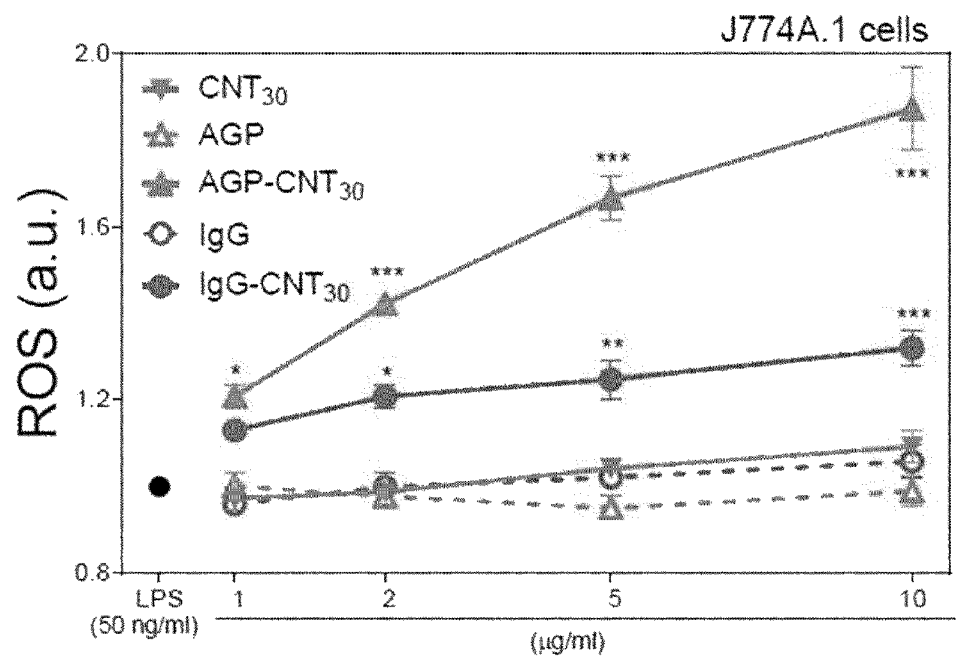
FIG. 6A shows graphs illustrating the analysis results of the ROS level of J774A.1 cells, in which (a) shows a graph illustrating the analysis results of the ROS level of J774A.1 cells due to immunogenic proteins (AGP and IgG) in CNT (30 nm).
Figure 6B:
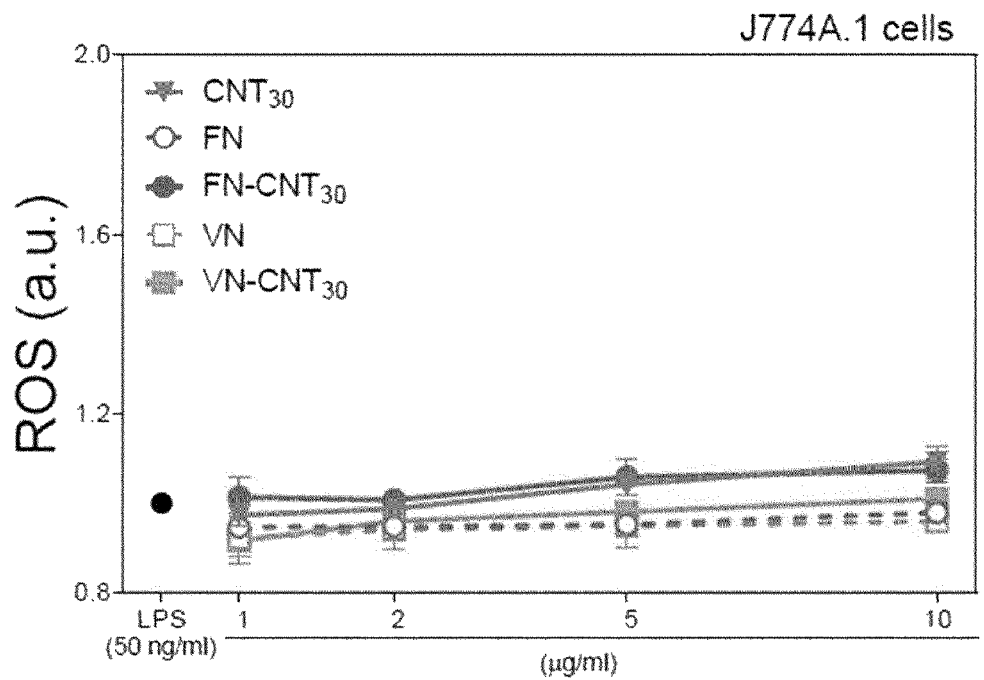
FIG. 6B shows graphs illustrating the analysis results of the ROS level of J774A.1 cells, in which shows a graph illustrating analysis results of the ROS level of J774A.1 cells due to non-immunogenic proteins (FN and VN) in CNT (30 nm).
Figure 7A:
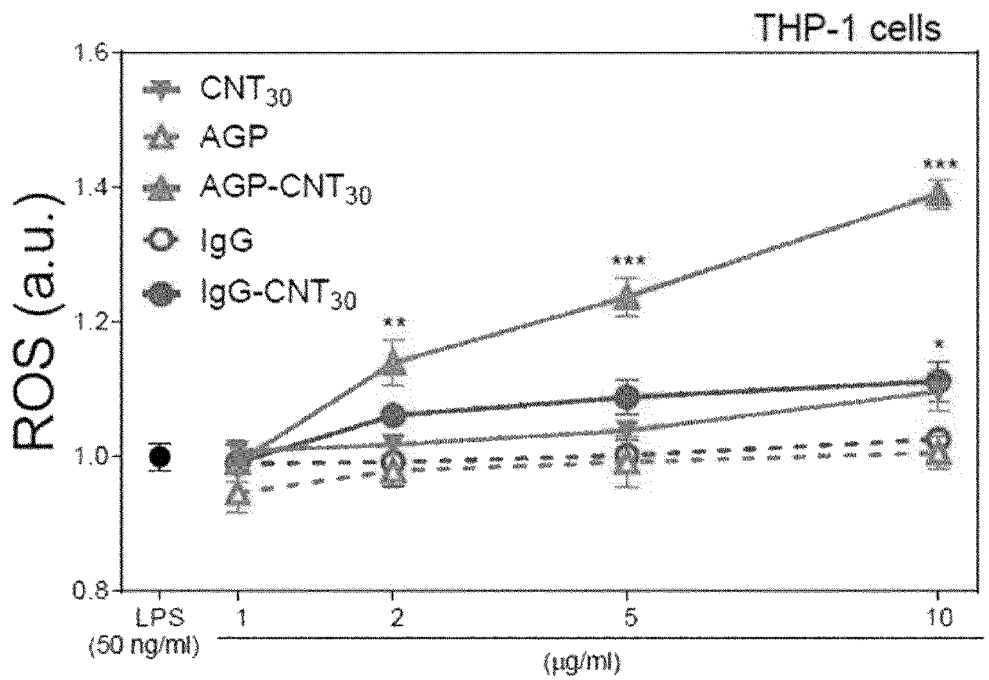
FIG. 7A shows graphs illustrating the analysis results of the ROS level of THP-1 cells, in which shows a graph illustrating the analysis results of the ROS level of THP-1 cells due to immunogenic proteins (AGP and IgG) in CNT (30 nm).
Figure 7B:
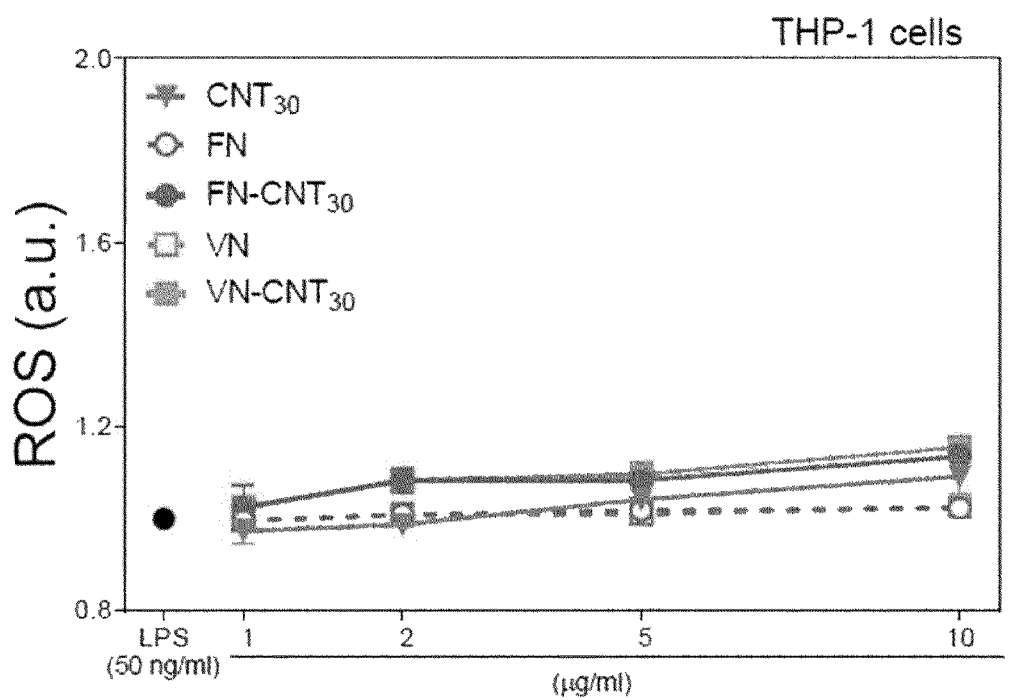
FIG. 7B shows graphs illustrating the analysis results of the ROS level of THP-1 cells, in which shows a graph illustrating analysis results of the ROS level of THP-1 cells due to non-immunogenic proteins (FN and VN) in CNT (30 nm).

As a result, it was confirmed that both macrophages and monocytes induce activation of ROS, which is an inflammatory mediator. In particular, although immunogenic coronas (AGP-CNTs and IgG-CNTs) showed significant concentration-dependent ROS production, non-immunogenic coronas (FN and VN) did not induce notable ROS production by LPS-treated macrophages and monocytes (FIGS. 6A, 6B, 7A and 7B). In addition, the CNT10 with a small diameter generated more ROS than the CNT30 with a large diameter and increased secretion of proinflammatory cytokines compared to the CNT with a large diameter. In addition, non-immunogenic proteins (FN and VN) did not show a significant change in ROS production by macrophages and monocytes (FIGS. 6A, 6B, 7A and 7B). Although significant secretion of major proinflammatory cytokines (e.g., Tnf, Il1b, and Il6) by the immunogenic coronas (AGP and IgG) around CNTs was observed in macrophages (J774A.1), no secretion of proinflammatory cytokines by non-immunogenic coronas (FN and VN) was observed (FIGS. 5B-5D).

In addition, the CNT10 with a smaller diameter induced more proinflammatory cytokines than the CNT30 with a larger diameter. Therefore, the above results suggest that the structural change in the immunogenic plasma protein corona has a significant effect on subsequent immunotoxicity, due to production of ROS and pro-inflammatory cytokines (FIGS. 5A to 5D). In contrast, the non-immunogenic protein corona showed a minor change in the secondary structure, and this change was similarly shown in ROS production and secretion of proinflammatory cytokines (FIGS. 6A, 6B, 7A and 7B).

Experimental Example 5: Analysis of Proinflammatory Cytokines

The spleen, an organ of a reticuloendothelial system, is part of the immune system consisting of phagocytes in the reticuloendothelial tissue (V. Bronte, et al., *Nat Immunol*, 16, 343. 2015). The spleen is very sensitive to damage by xenobiotics in vitro, and the lymphocyte population of the spleen is essential for the immune response. In order to examine the immunotoxicity of immune-induced corona in CNTs, the present inventors have performed an in vivo experiment using 5 mg/kg/day (protein concentration) and the same was administered by intravenous injection twice every three days.

Figure 8A:
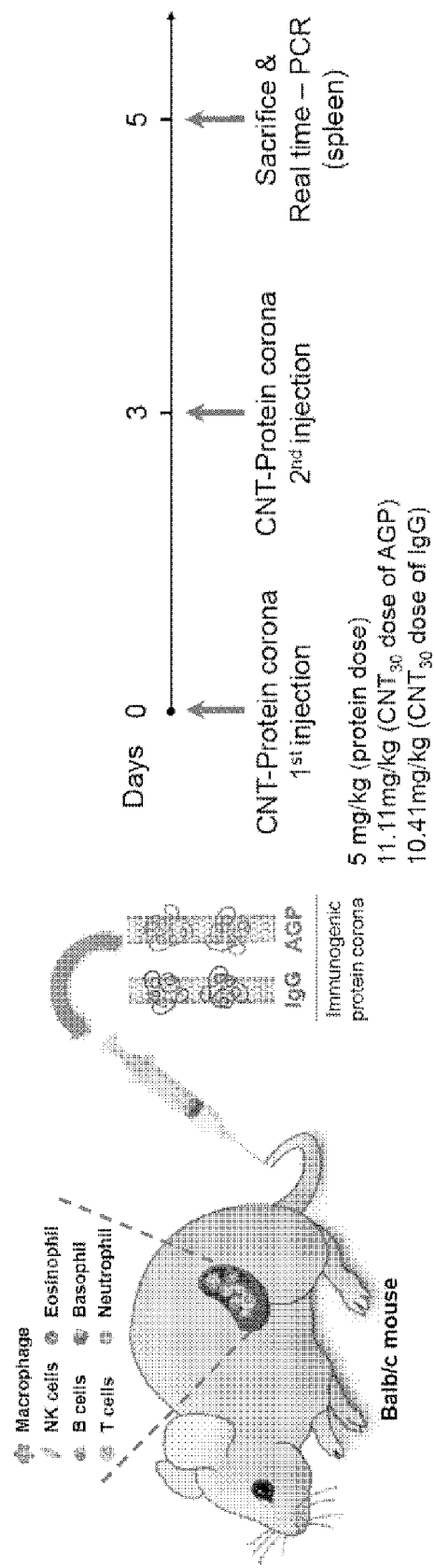
FIG. 8A shows an experimental procedure for mice and results using CNTs to which the immunogenic protein of the present disclosure is bound, in which shows an intravenous injection (IV) protocol for an immunogenic protein corona (IgG and AGP).
Figure 8B:
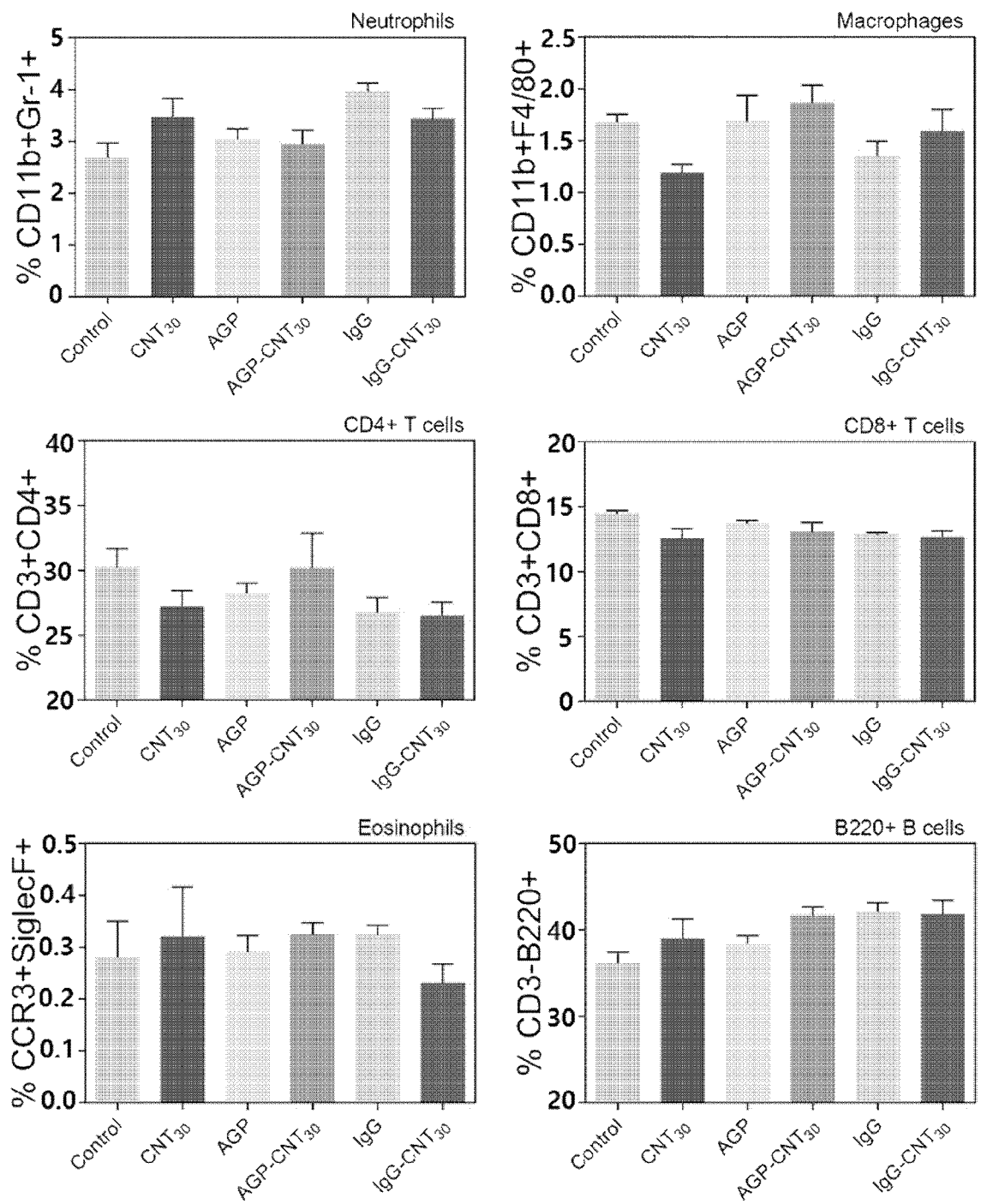
FIG. 8B shows an experimental procedure for mice and results using CNTs to which the immunogenic protein of the present disclosure is bound, in which shows a graph illustrating the FACS analysis results of immune cells (neutrophils, macrophages, Th cells, Tc cells, B cells, and eosinophils) isolated from the spleen tissue of the mice.
Figure 9A:
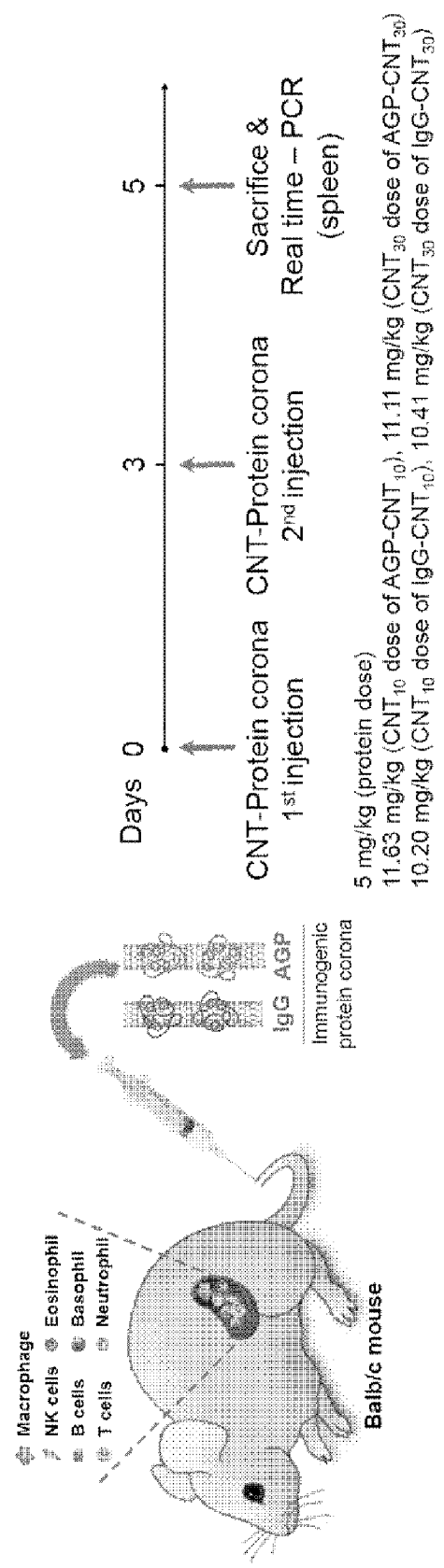
FIG. 9A shows observation results of an immune response in vivo due to the immunogenic protein corona surrounding CNTs, in which shows an intravenous injection (IV) protocol for an immunogenic protein corona.
Figure 9B:
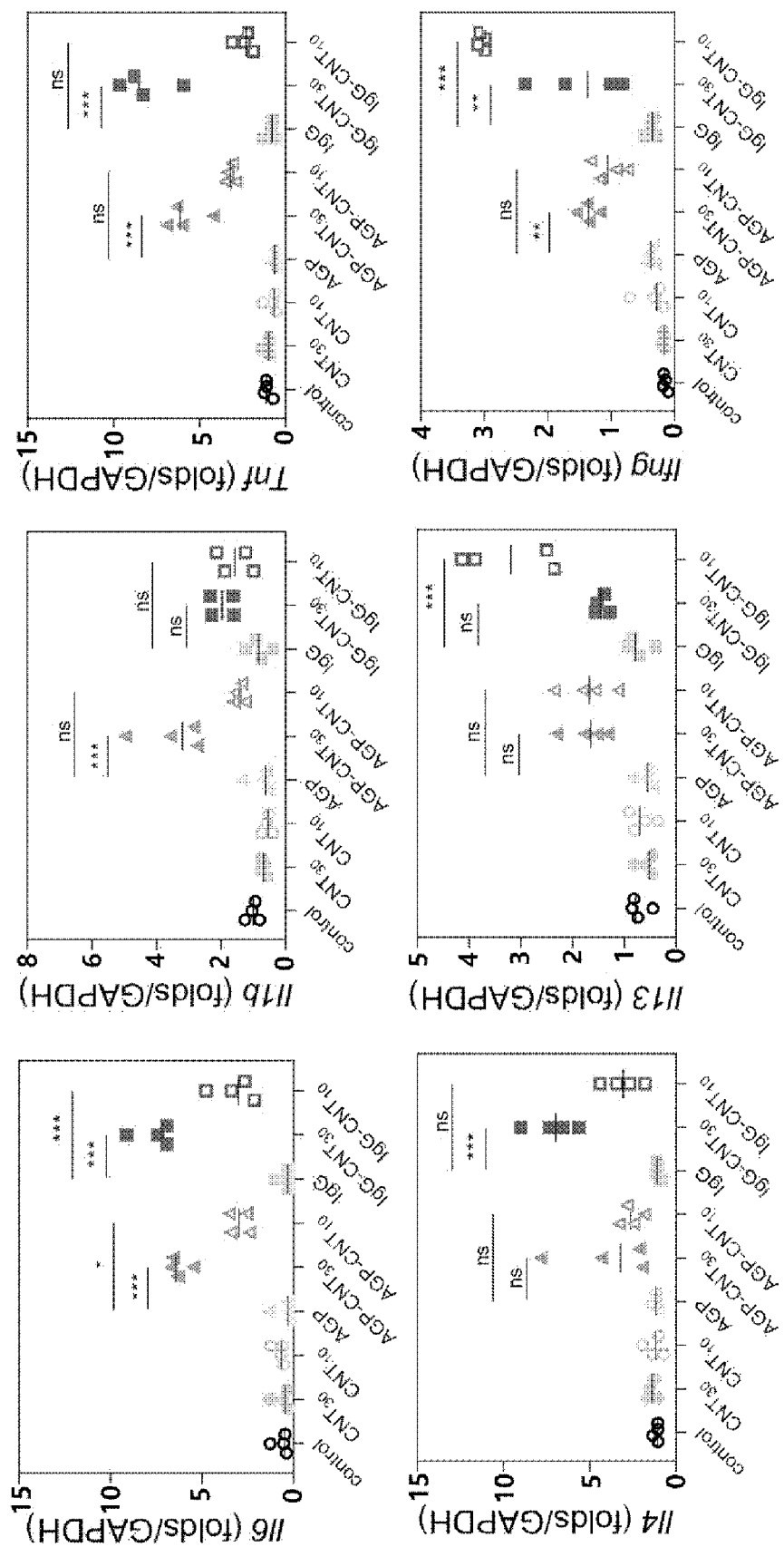
FIG. 9B shows observation results of an immune response in vivo due to the immunogenic protein corona surrounding CNTs, in which shows graphs illustrating the analysis results of the relative gene expression (mRNA) of innate inflammatory cytokines (Il6, Il1b, Tnf, Il4, Il13, and Ifng) in the spleen after treatment with the immunogenic protein corona surrounding CNTs.
Figure 10A:
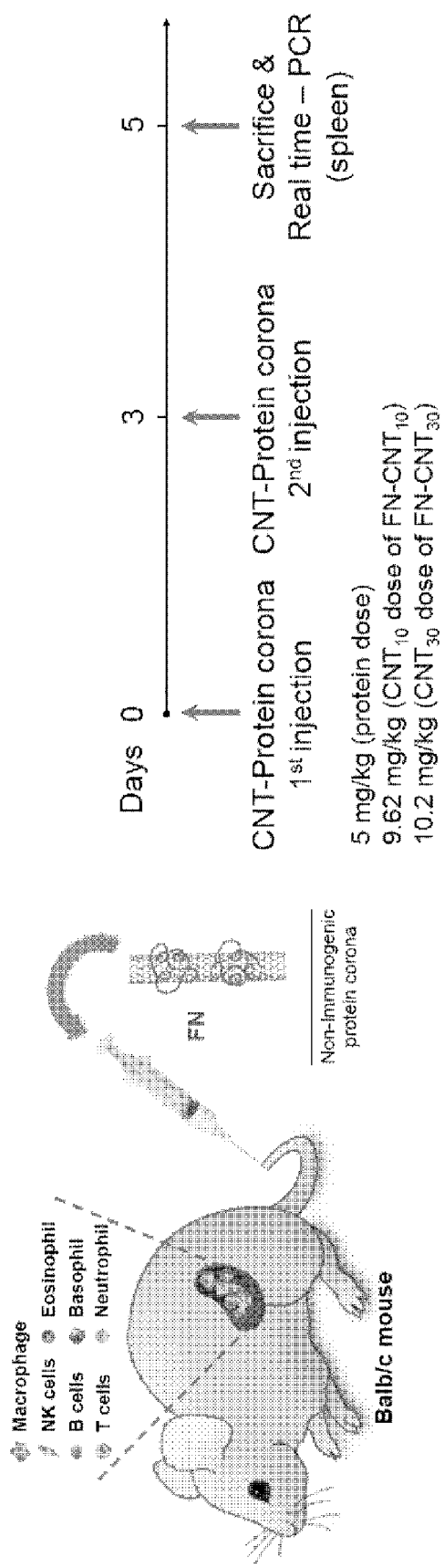
FIG. 10A shows observation results of an immune response in vivo due to the non-immunogenic protein corona (FN-CNT10 and FN-CNT30) surrounding CNTs, in which shows an intravenous injection (IV) protocol for a non-immunogenic protein corona.
Figure 10B:
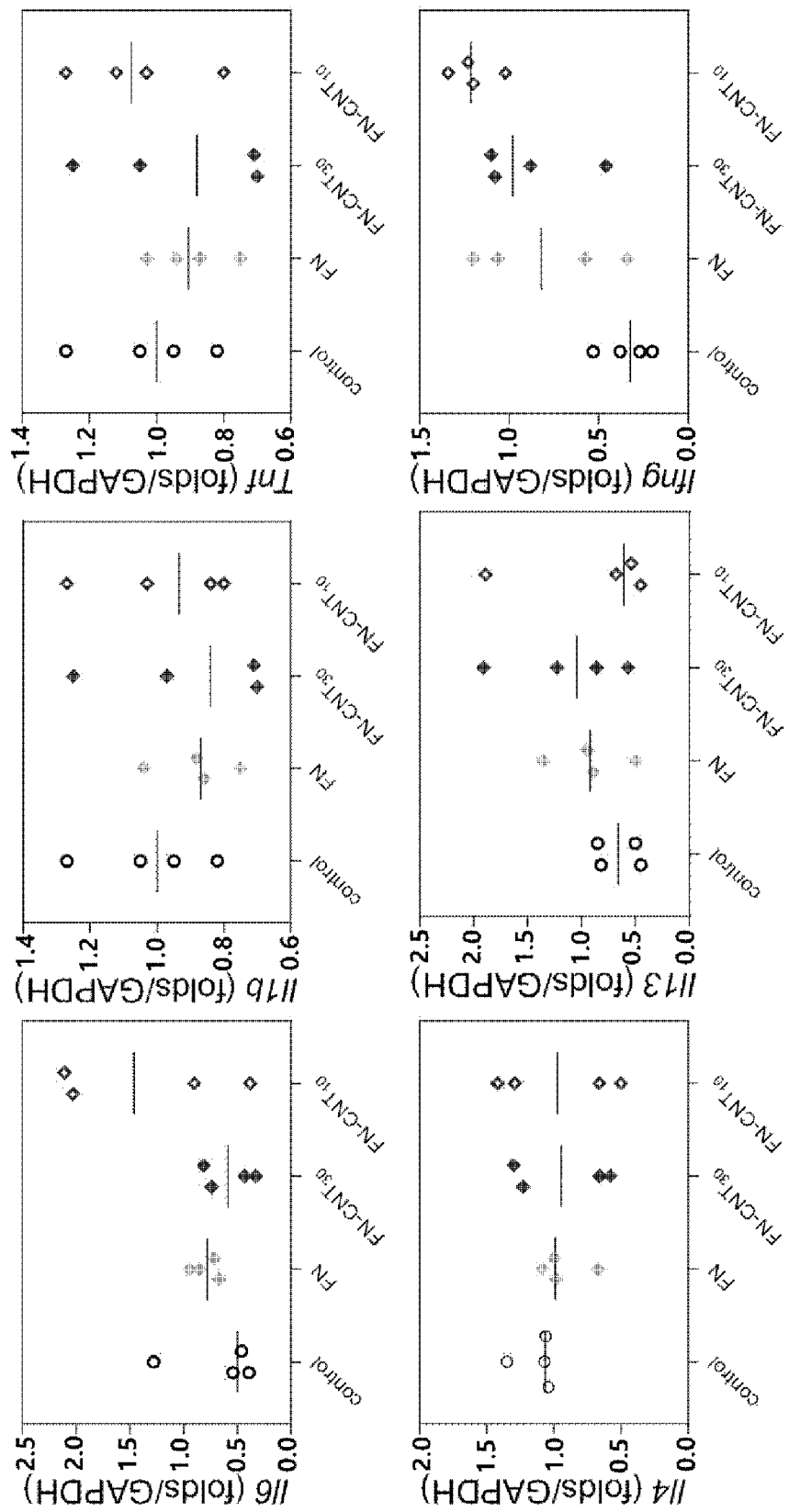
FIG. 10B shows observation results of an immune response in vivo due to the non-immunogenic protein corona (FN-CNT10 and FN-CNT30) surrounding CNTs, in which shows graphs illustrating the analysis results of the relative gene expression (mRNA) of innate inflammatory cytokines (Il6, Il1b, Tnf, Il4, Il13, and Ifng) in the spleen after treatment with the non-immunogenic protein corona surrounding CNTs.

As a result, no significant changes in neutrophils, macrophages and eosinophils were observed in the spleen after administration of both AGP-CNT30 and IgG-CNT30 (FIGS. 8A and 8B). In addition, as a result of analysis of the changes in innate inflammatory cytokines (Tnf, Il1b, Il6, Il4, Il13, and Ifng) in the spleen (FIGS. 9A and 9B), the immunogenic protein corona (both 10 nm and 30 nm NT for AGP-CNT and IgG-CNT) mainly induced innate inflammatory immune responses, such as upregulation of Tnf, Il1b, Il6, Il4, Il13, and Ifng (FIG. 9B). In addition, the different immune responses between the immunogenic protein coronas surrounding CNT10 and CNT30 were shown to be insignificant (FIG. 9B). These results suggest that the size of CNTs is not an important factor affecting the subsequent innate immune response in vivo. FNCNTs (both 10 nm and 30 nm) did not induce production of significant proinflammatory cytokines in the spleen (FIGS. 10A and 10B). Although the interaction of PEGgylated CNTs and individual proteins (AGP and IgG) in the spleen did not induce expression of inflammatory cytokines, the immunogenic protein coronas surrounding the CNTs induced a significant immune response (FIGS. 9B, 10A and 10B). Therefore, while the altered structural changes in the immunogenic plasma proteins significantly affected the subsequent inflammation, the non-immunogenic proteins did not induce production of notable proinflammatory markers in the spleen.

In conclusion, the carbon nanotubes coated on the surface of the immunogenic plasma proteins of the present disclosure can be functionalized as a protein corona with a targeting ability, and thereby used in diagnostic fields (e.g., sensitive targeted imaging) and as a therapeutic agent that selectively delivers cytotoxic substances (e.g., anticancer drugs and drugs) to diseased cells in the human body.

Although the present disclosure has been described with reference to the above-described Examples and Experimental Examples, these Examples and Experimental Examples are merely for illustrative purposes, and those of ordinary skill in the art would understand that various modifications and equivalent other Examples and Experimental Examples are possible therefrom. Therefore, the true technical protection scope of the present disclosure should be determined by the technical idea of the appended claims.

Effects of the Invention

According to one embodiment of the present disclosure established as described above, the drug delivery system of the present disclosure, in which the innate immune response is improved by the structural change in the immunogenic protein corona coated on the surface of carbon nanotubes, can be utilized for treatment of cancer and tumor due to its effective immune activity. Certainly, the scope of the present disclosure is not limited by these effects.

Although the drug delivery system with an enhanced immune activity function has been described with reference to the specific embodiments, it is not limited thereto. Therefore, it will be readily understood by those skilled in the art that various modifications and changes can be made thereto without departing from the spirit and scope of the present invention defined by the appended claims.

What is claimed is:

1. A composite nanoparticle in which an immunogenic plasma protein is coated on the surface of a nanoparticle, wherein the immunogenic protein is α1 acid glycoprotein (AGP) or immunoglobulin G (IgG), wherein the nanoparticle is a gold nanoparticle or a carbon nanotube, wherein the nanoparticle is a polyethylene glycol (PEG)-coated nanoparticle in which PEG is coated on the surface of the nanoparticle; and wherein unordered structure of the immunogenic protein is increased by interaction with the nanoparticle and inducing a significant immune response thereby.

2. An immunoactivity agent comprising the composite nanoparticle of claim 1.

3. A drug delivery system comprising the composite nanoparticle of claim 1.

4. A cancer treatment agent in which an anticancer agent is bound to the drug delivery system of claim 3.

5. The cancer treatment agent of claim 4, wherein the cancer is selected from the group consisting of liver cancer, colorectal cancer, uterine cervical cancer, kidney cancer, stomach cancer, prostate cancer, breast cancer, brain tumor, lung cancer, uterine cancer, colon cancer, bladder cancer, blood cancer, and pancreatic cancer.

6. The cancer treatment agent of claim 4, wherein the anticancer agent is doxorubicin, epirubicin, adriamycin, cis-platin, mitomycin-C, or daunomycin.

7. A method for treating cancer, comprising administering the cancer treatment agent of claim 4 to a subject having cancer.

* * * * *